(12) United States Patent
Urzhumov

(10) Patent No.: US 10,092,351 B2
(45) Date of Patent: Oct. 9, 2018

(54) MINIMALLY-INVASIVE TISSUE ABLATION USING HIGH CONTRAST ELECTRIC FIELDS

(71) Applicant: Elwha LLC, Bellevue, WA (US)

(72) Inventor: Yaroslav A. Urzhumov, Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 761 days.

(21) Appl. No.: 14/619,393

(22) Filed: Feb. 11, 2015

(65) Prior Publication Data

US 2016/0228183 A1 Aug. 11, 2016

(51) Int. Cl.
*A61B 18/12* (2006.01)
*A61B 18/18* (2006.01)
*A61B 18/00* (2006.01)

(52) U.S. Cl.
CPC .... *A61B 18/18* (2013.01); *A61B 2018/00577* (2013.01); *A61B 2018/00732* (2013.01)

(58) Field of Classification Search
CPC .......... A61B 18/18; A61B 2018/00577; A61B 2018/00732
See application file for complete search history.

(56) References Cited

U.S. PATENT DOCUMENTS 4,712,069 A * 12/1987 Kemner ............. G01R 33/3678
324/318
5,317,265 A * 5/1994 Weinstock ............. G01R 33/46
324/312

(Continued)

FOREIGN PATENT DOCUMENTS

WO WO 01/19451 A1 3/2001

OTHER PUBLICATIONS

Caglayan et al.; "Experimental Observation of Subwavelength Localization Using Metamaterial-Based Cavities"; Optics Letters; Jan. 1, 2009; pp. 88-90; vol. 34, No. 1; Optical Society of America.

(Continued)

*Primary Examiner* — Daniel Fowler
(74) *Attorney, Agent, or Firm* — Foley & Lardner LLP

(57) ABSTRACT

Described embodiments include a system and a method. A system includes an electromagnetic structure having a surface and a radiofrequency electromagnetic field source. The field source includes electronically controllable, artificially structured electromagnetic unit cells configured to create quasi-static electromagnetic fields within the electromagnetic structure. Each unit cell is responsive to a control signal. A selector circuit selects a quasi-static electromagnetic field pattern creating a high contrast electric field in a subwavelength electromagnetic cavity and is defined by the surface of the electromagnetic structure and an exterior surface of a perturbing object. The high contrast electric field has a power density that is localized to a volume adjoining the exterior surface of the perturbing object. A field pattern implementation circuit generates the control signal assigning electromagnetic field characteristic to each of the electromagnetic unit cells. The assigned radiofrequency electromagnetic field characteristics collectively creating the selected quasi-static electromagnetic field pattern.

43 Claims, 12 Drawing Sheets

(56) References Cited

U.S. PATENT DOCUMENTS

| | | | |
|---|---|---|---|
| 5,564,421 A * | 10/1996 | Ehnholm | G01R 33/345 |
| | | | 324/316 |
| 7,091,457 B2 | 8/2006 | Gregoire et al. | |
| 8,796,886 B2 | 8/2014 | Tan | |
| 2004/0064031 A1 * | 4/2004 | Dean | G01R 33/3804 |
| | | | 600/410 |
| 2007/0027532 A1 | 2/2007 | Wang et al. | |
| 2008/0033569 A1 | 2/2008 | Ferren et al. | |
| 2008/0192331 A1 * | 8/2008 | Wang | B82Y 20/00 |
| | | | 359/315 |
| 2009/0284083 A1 | 11/2009 | Karalis et al. | |
| 2013/0301983 A1 | 11/2013 | Mazumder et al. | |

OTHER PUBLICATIONS

Ciraci et al.; "Probing the Ultimate Limits of Plasmonic Enhancement"; Science; Aug. 31, 2012; pp. 1072-1074; vol. 337.

"Connected Space"; Wikipedia; Bearing a date of Aug. 3, 2014; 6 Total Pages; located at: http://en.wikipedia.org/wiki/Connected_space.

Das et al.; "Theory of Welding of Metallic Parts in Microwave Cavity Applicator"; Fundamental J. Modern Physics; Bearing a date of Sep. 21, 2012; pp. 125-155; vol. 3, Issue 2; Fundamental Research and Development International.

"Electromagnetic Waves in a Cubical Cavity"; Rayleigh-Jeans Law Development; Created on Oct. 30, 2014; 6 Total Pages; located at: http://hyperphysics.phy-astr.gsu.edu/hbase/quantum/rayj.html.

Errede, Steven; "Lecture Notes 10.5—EM Standing Waves in Resonant Cavities"; Fall Semester 2011, Created on Nov. 4, 2014; pp. 1-15; Department of Physics, University of Illinois at Urbana-Champaign.

Gonzalez et al.; "Circuital Model for the Maxwell Fish Eye Perfect Drain"; Bearing a date of Mar. 12, 2012; 15 Total Pages.

Gonzalez et al.; "Perfect Drain for the Maxwell Fish Eye Lens"; New Journal of Physics; Feb. 2011; 11 Total Pages; vol. 13.

Hanninen et al.; "Realization of Generalized Soft-and-Hard Boundary"; Progress in Electromagnetics Research; Bearing a date of 2006, Created on Nov. 5, 2014; pp. 317-333; vol. 64.

Karalis et al.; "Efficient Wireless Non-Radiative Mid-Range Energy Transfer"; Annals of Physics; Apr. 27, 2007; pp. 34-48; vol. 323; Elsevier Inc.

Kildal, Per-Simon; "Artificially Soft and Hard Surfaces in Electromagnetics"; IEEE Transactions of Antennas and Propagation; Oct. 1990; pp. 1537-1544; vol. 38, No. 10; IEEE.

Kildal, P.-S.; "Definition of Artificially Soft and Hard Surfaces for Electromagnetic Waves"; Electronics Letters; Feb. 4, 1988; pp. 168-170; vol. 24, No. 3.

Korobkin et al.; "Mid-Infrared Metamaterial Based on Perforated SiC Membrane: Engineering Optical Response Using Surface Phonon Polaritons"; Applied Physics A.; Jun. 12, 2007; pp. 605-609; vol. 88; Springer-Verlag.

Labanc; Anton; "Electrical Axes of TESLA-Type Cavities"; TESLA Report Jan. 2008; Jan. 2008; pp. 1-23.

Le et al.; "Metallic Nanoparticle Arrays: A Common Substrate for Both Surface-Enhanced Raman Scattering and Surface-Enhanced Infrared Absorption"; ACS Nano; Mar. 21, 2008; pp. 707-718; vol. 2, No. 4; American Chemical Society.

Markel et al.; "Small-Particle Composites. I. Linear Optical Properties"; Physical Review B.; Feb. 1, 1996; pp. 2425-2436; vol. 53, No. 5; American Physical Society.

Nasserdine et al.; "Field Measurements Within a Large Resonant Cavity Based on the Perturbation Theory"; Progress in Electromagnetics Research B; Nov. 21, 2013; pp. 1-20; vol. 57.

Penninkhof et al.; "Optical Cavity Modes in Gold Shell Colloids"; Journal of Applied Physics ; Jun. 18, 2008; pp. 123105-1 to 123105-7; vol. 103; American Institute of Physics.

Sandu, Titus; "Eigenmode Decomposition of the Near-Field Enhancement in Localized Surface Plasmon Resonances of Metallic Nanoparticles"; Plasmonics; May 29, 2013; pp. 1-23; vol. 8.

Shvets et al.; "Engineering the Electromagnetic Properties of Periodic Nanostructures Using Electrostatic Resonances"; Physical Review Letters; Dec. 10, 2004; pp. 243902-1 to 243902-4; vol. 93; The American Physical Society.

Sun et al.; "Can Maxwell's Fish Eye Lens Really Give Perfect Imaging?"; Progress in Electromagnetics Research; Sep. 23, 2010; pp. 307-322; vol. 108.

Sun et al.; "On Subwavelength Imaging with Maxwell's Fish Eye Lens"; Created on Feb. 5, 2015; 10 Total Pages.

Worasawate et al.; "Electromagnetic Resonances and Field Distributions of a Chiral Filled Spherical Perfectly Conducting Cavity"; Progress in Electromagnetics Research; Bearing a date of 2008, Created on Oct. 30, 2014; pp. 77-94; vol. 82.

Yuan et al.; "Zero Loss Magnetic Metamaterials Using Powered Active Unit Cells"; Optics Express; Aug. 31, 2009; pp. 16135-16143; vol. 17, No. 18.

* cited by examiner

FIG. 5
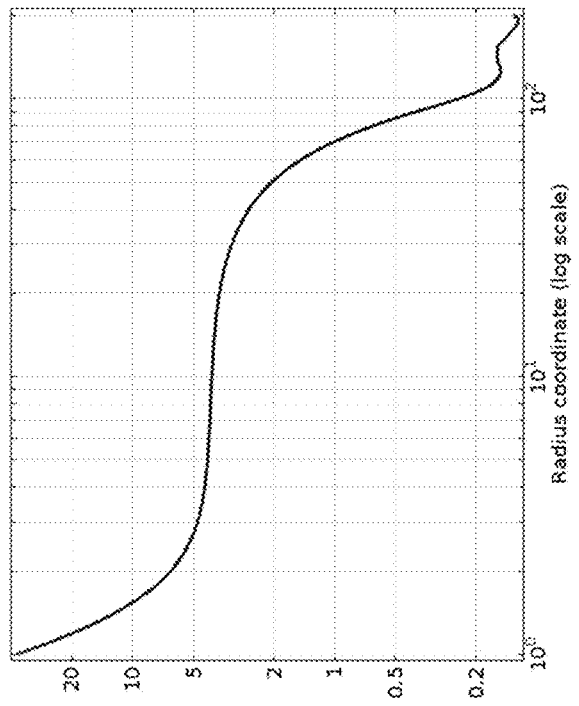
FIG. 4A (optimized)
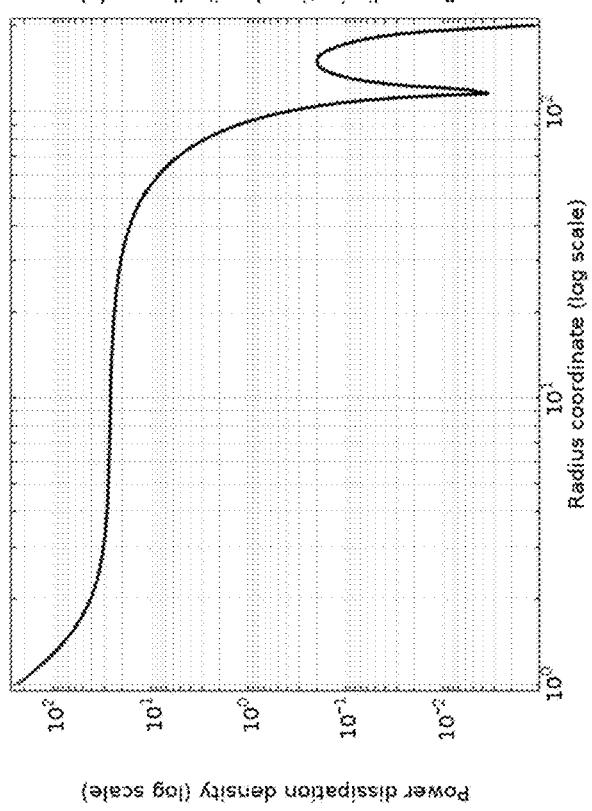
FIG. 2A (eignmode)

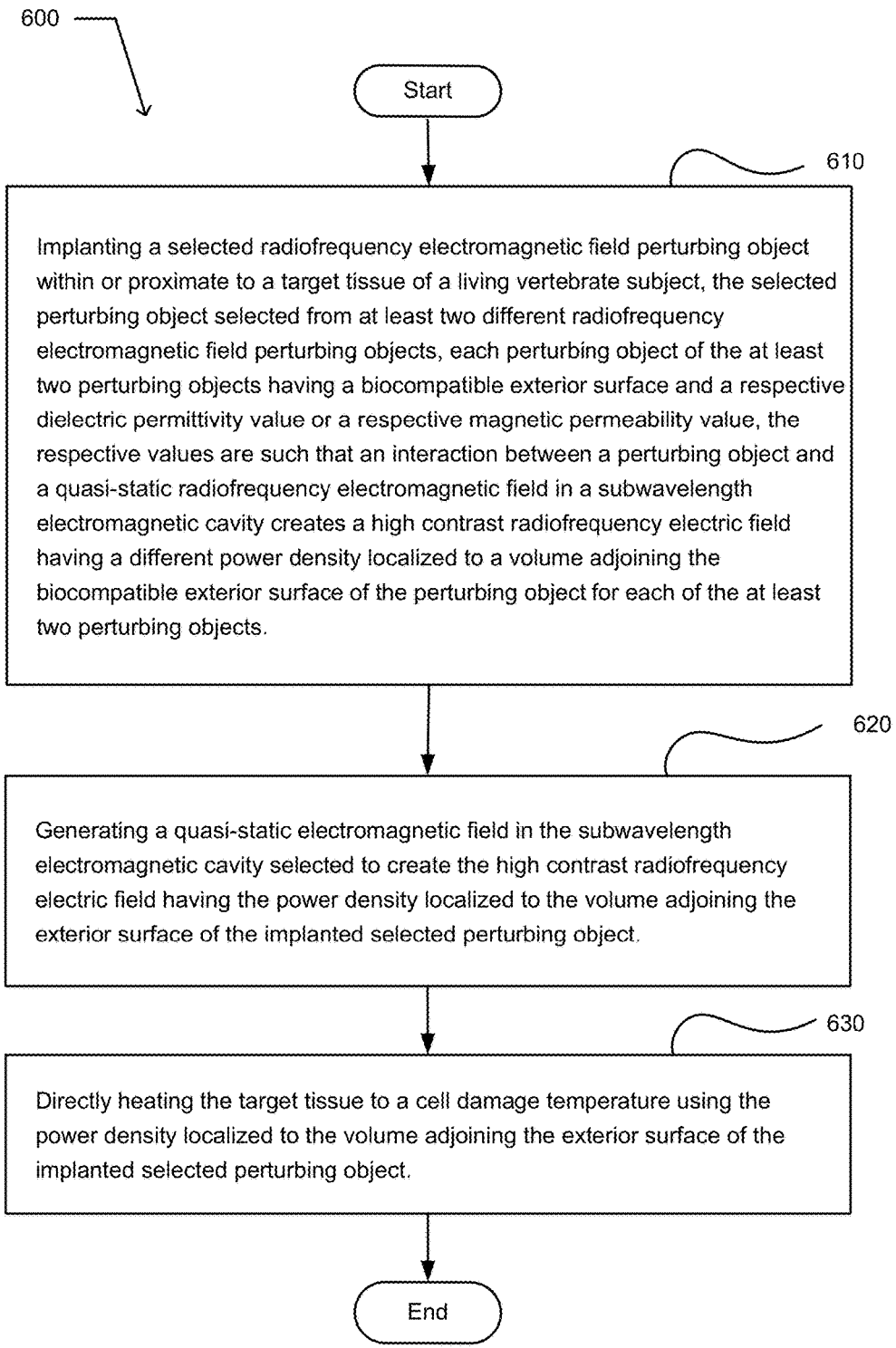

MINIMALLY-INVASIVE TISSUE ABLATION USING HIGH CONTRAST ELECTRIC FIELDS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

For example, and without limitation, an embodiment of the subject matter described herein includes a system. The system includes an electromagnetic structure having a surface that includes a radiofrequency electromagnetic field source. The radiofrequency electromagnetic field source includes at least two electronically controllable, artificially structured electromagnetic unit cells configured to create quasi-static radiofrequency electromagnetic fields within the electromagnetic structure. Each unit cell is respectively responsive to a control signal. The system includes a selector circuit configured to select a quasi-static electromagnetic field pattern creating a high contrast radiofrequency electric field in a subwavelength electromagnetic cavity is defined at least in part by the surface of the electromagnetic structure and an exterior surface of a perturbing object. The high contrast radiofrequency electric field has a power density localized to a volume adjoining the exterior surface of the perturbing object. The system includes a field pattern implementation circuit configured to generate the control signal assigning a respective radiofrequency electromagnetic field characteristic to each of the at least two electronically controllable, artificially structured electromagnetic unit cells. The respective assigned radiofrequency electromagnetic field characteristics collectively creating the selected quasi-static radiofrequency electromagnetic field pattern within the electromagnetic cavity. In an embodiment, the surface of the structure includes an inner surface of the structure.

In an embodiment, the system includes a radiofrequency electromagnetic wave conducting structure configured to distribute radiofrequency electromagnetic waves to the at least two artificially structured electromagnetic unit cells. In an embodiment, the system includes a radiofrequency electromagnetic wave generator or synthesizer configured to generate radiofrequency electromagnetic waves in at least a portion of the 1 MHz-1 GHz range.

For example, and without limitation, an embodiment of the subject matter described herein includes a method. The method includes selecting a quasi-static electromagnetic field pattern creating a high contrast radiofrequency electric field in a subwavelength electromagnetic cavity. The high contrast radiofrequency electric field including a power density localized to a volume adjoining an exterior surface of a perturbing object implanted within or proximate to a target tissue of a living vertebrate subject. The subwavelength electromagnetic cavity is defined at least in part by a surface of an electromagnetic structure and the exterior surface of the perturbing object. The method includes assigning a respective radiofrequency electromagnetic field characteristic to each of at least two electronically controllable, artificially structured electromagnetic unit cells associated with the surface of the electromagnetic structure. The respective assigned radiofrequency electromagnetic field characteristics collectively creating the selected quasi-static electromagnetic field pattern within the electromagnetic cavity. The method includes implementing the assigned respective radiofrequency electromagnetic field characteristic in each of the at least two electronically controllable, artificially structured electromagnetic unit cells.

In an embodiment, the method includes thermally ablating the volume of the target tissue of the living vertebrate subject adjoining the exterior surface of the implanted perturbing object. In an embodiment, the method includes creating the selected quasi-static electromagnetic field pattern. In an embodiment, the method includes distributing radiofrequency electromagnetic waves having a frequency in at least a portion of the 1 MHz-100 MHz range to the at least two artificially structured electromagnetic unit cells. In an embodiment, the method includes implanting the perturbing object within or proximate to the target tissue of the living vertebrate subject. In an embodiment, the method includes positioning the perturbing object within a near-field coupling region of the subwavelength electromagnetic structure having an inner surface that includes the radiofrequency electromagnetic field source.

For example, and without limitation, an embodiment of the subject matter described herein includes a system. The system includes means for selecting a quasi-static electromagnetic field pattern creating a high contrast radiofrequency electric field in a subwavelength electromagnetic cavity. The high contrast radiofrequency electric field including a power density localized to a volume adjoining an exterior surface of a perturbing object implanted within or proximate to a target tissue of a living vertebrate subject. The subwavelength electromagnetic cavity is defined at least in part by an inner surface of an electromagnetic structure and the exterior surface of the perturbing object. The system includes means for assigning a respective radiofrequency electromagnetic field characteristic to each of at least two electronically controllable, artificially structured electromagnetic unit cells associated with the surface of the electromagnetic structure. The respective assigned radiofrequency electromagnetic field characteristics collectively creating the selected quasi-static electromagnetic field pattern within the electromagnetic cavity. The system includes means for implementing the assigned respective radiofrequency electromagnetic field characteristic in each of the at least two electronically controllable, artificially structured electromagnetic unit cells.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 5 illustrates a side by side log-log comparison between the power density profile of a selected dipolar eigenmode of the MARAUC system illustrated by FIG. 2A, and the field distribution produced as a result of an optimized excitation in the MARUAC system illustrated by FIG. 4A;

FIG. 12 illustrates another example operational flow.

DETAILED DESCRIPTION

Figure 1:
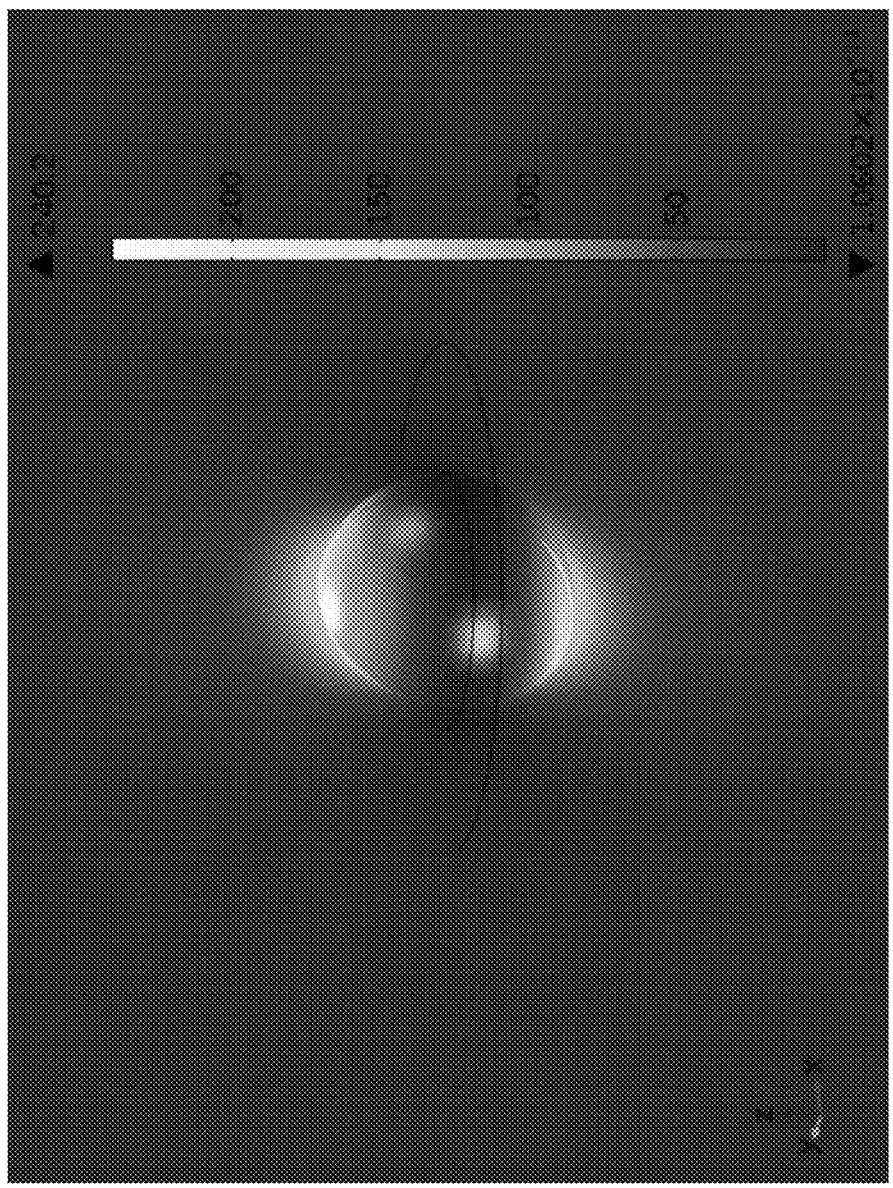
FIG. 1 illustrates an example modeled embodiment of a system that includes a small particle inside a volume of human tissue, and surrounded a quasi-static radiofrequency electromagnetic field generated by a metamaterial aperture with randomly addressable unit cells which has no direct contact with the tissue.

This application makes reference to technologies described more fully in U.S. patent application Ser. No. 14/257,175, entitled SUB-NYQUIST HOLOGRAPHIC APERTURE ANTENNA CONFIGURED TO DEFINE SELECTABLE, ARBITRARY COMPLEX ELECTROMAGNETIC FIELDS, naming Pai-Yen Chen et al. as inventors, filed on Apr. 21, 2014, is related to the present application. That application is incorporated by reference herein, including any subject matter included by reference in that application.

This application makes reference to technologies described more fully in U.S. patent application Ser. No. 14/257,187, entitled SUB-NYQUIST HOLOGRAPHIC APERTURE ANTENNA CONFIGURED TO DEFINE SELECTABLE, ARBITRARY COMPLEX ELECTROMAGNETIC FIELDS, naming Pai-Yen Chen et al. as inventors, filed on Apr. 21, 2014, is related to the present application. That application is incorporated by reference herein, including any subject matter included by reference in that application.

This application makes reference to technologies described more fully in U.S. patent application Ser. No. 14/257,386, entitled SYSTEM WIRELESSLY TRANSFERRING POWER TO A TARGET DEVICE OVER A TESTED TRANSMISSION PATHWAY, naming Pai-Yen Chen et al. as inventors, filed on Apr. 21, 2014, is related to the present application. That application is incorporated by reference herein, including any subject matter included by reference in that application.

This application makes reference to technologies described more fully in U.S. patent application Ser. No. 14/257,415, entitled SYSTEM WIRELESSLY TRANSFERRING POWER TO A TARGET DEVICE OVER A MODELED TRANSMISSION PATHWAY WITHOUT EXCEEDING A RADIATION LIMIT FOR HUMAN BEINGS, naming Pai-Yen Chen et al. as inventors, filed on Apr. 21, 2014, is related to the present application. That application is incorporated by reference herein, including any subject matter included by reference in that application.

This application makes reference to technologies described more fully in U.S. patent application Ser. No. 12/286,740, now U.S. Pat. No. 8,168,930, entitled BEAM POWER FOR LOCAL RECEIVERS, naming Roderick A. Hyde et al. as inventors, filed on Sep. 30, 2008, is related to the present application. That application is incorporated by reference herein, including any subject matter included by reference in that application.

This application makes reference to technologies described more fully in U.S. patent application Ser. No. 12/286,737, now U.S. Pat. No. 8,058,609, entitled BEAM POWER WITH MULTIPOINT BROADCAST, naming Roderick A. Hyde et al. as inventors, filed on Sep. 30, 2008, is related to the present application. That application is incorporated by reference herein, including any subject matter included by reference in that application.

This application makes reference to technologies described more fully in U.S. patent application Ser. No. 12/286,755, now U.S. Pat. No. 8,803,053, entitled BEAM POWER WITH MULTIPOINT RECEPTION, naming Roderick A. Hyde et al. as inventors, filed on Sep. 30, 2008, is related to the present application. That application is incorporated by reference herein, including any subject matter included by reference in that application.

This application makes reference to technologies described more fully in U.S. patent application Ser. No. 12/286,741, now U.S. Pat. No. 7,786,419, entitled BEAM POWER WITH BEAM REDIRECTION, naming Roderick A. Hyde et al. as inventors, filed on Sep. 30, 2008, is related to the present application. That application is incorporated by reference herein, including any subject matter included by reference in that application.

This application makes reference to technologies described more fully in U.S. Patent Application No. 61/455,171, entitled SURFACE SCATTERING ANTENNAS, naming Nathan Kundtz as inventor, filed Oct. 15, 2010, is related to the present application. That application is incorporated by reference herein, including any subject matter included by reference in that application.

This application makes reference to technologies described more fully in U.S. patent application Ser. No. 13/317,338, entitled SURFACE SCATTERING ANTENNAS, naming Adam Bily et al. as inventors, filed Oct. 14, 2011, is related to the present application. That application is incorporated by reference herein, including any subject matter included by reference in that application.

This application makes reference to technologies described more fully in U.S. patent application Ser. No. 13/838,934, entitled SURFACE SCATTERING ANTENNA IMPROVEMENTS, naming Adam Bily et al. as inventors, filed Mar. 15, 2013, is related to the present application. That application is incorporated by reference herein, including any subject matter included by reference in that application.

This application makes reference to technologies described more fully in U.S. patent application Ser. No. 14/102,253, entitled SURFACE SCATTERING REFLECTOR ANTENNA, naming Jeffrey A. Bowers et al. as inventors, filed Dec. 10, 2013, is related to the present application. That application is incorporated by reference herein, including any subject matter included by reference in that application.

This application makes reference to technologies described more fully in U.S. patent application Ser. No. 14/226,213, entitled SURFACE SCATTERING ANTENNA ARRAY, naming Jeffrey A. Bowers et al. as inventors, filed Mar. 26, 2014, is related to the present application. That application is incorporated by reference herein, including any subject matter included by reference in that application.

This application makes reference to technologies described more fully in U.S. patent application Ser. No. 14/334,368, entitled ARTIFICIALLY STRUCTURED $B_1$ MAGNETIC FIELD GENERATOR FOR MRI AND NMR DEVICES, naming Tom Driscoll et al. as inventors, filed Jul. 17, 2014, is related to the present application. That application is incorporated by reference herein, including any subject matter included by reference in that application.

This application makes reference to technologies described more fully in U.S. patent application Ser. No. 14/334,398, entitled ARTIFICIALLY STRUCTURED UNIT CELLS PROVIDING LOCALIZED $B_1$ MAGNETIC FIELDS FOR MRI AND NMR DEVICES, naming Tom Driscoll et al. as inventors, filed Jul. 17, 2014, is related to the present application. That application is incorporated by reference herein, including any subject matter included by reference in that application.

This application makes reference to technologies described more fully in U.S. patent application Ser. No. 14/334,424, entitled ELECTRONICALLY CONTROLLABLE GROUPS OF ARTIFICIALLY STRUCTURED UNIT CELLS PROVIDING LOCALIZED $B_1$ MAGNETIC FIELDS FOR MRI AND NMR DEVICES, naming Tom Driscoll et al. as inventors, filed Jul. 17, 2014, is related to the present application. That application is incorporated by reference herein, including any subject matter included by reference in that application.

This application makes reference to technologies described more fully in U.S. patent application Ser. No. 14/334,450, entitled CANCELLATION OF AN ELECTRIC FIELD COMPONENT OF A MAGNETIC FIELD GENERATED BY ARTIFICIALLY STRUCTURED ELECTROMAGNETIC UNIT CELLS, naming Tom Driscoll et al. as inventors, filed Jul. 17, 2014, is related to the present application. That application is incorporated by reference herein, including any subject matter included by reference in that application.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

An embodiment of a system includes electronically controllable, randomly addressable, artificially structured electromagnetic unit cells. In an embodiment, the unit cells are configured as a metamaterial aperture with randomly addressable unit cells (MARAUC) that can create a quasi-static alternating electric and/or magnetic field configurations with highly localized hot spots of energy density, when assisted by an embedded perturbing object. The unit cells are configured to create quasi-static radiofrequency electromagnetic fields within a near-field coupling region of a sub-wavelength electromagnetic resonator structure. This configuration enables thermal ablation in controlled, small volumes of tissue situated at any necessary depths in the body (up to 10-20 cm) in a minimally invasive fashion. Minimally invasive ablation includes an ablation protocol that does not require incisions in the surrounding tissues, or having to insert electrodes or catheters to access the site. The locus of ablation is defined by the position of a small (for example, 100 micron to 1 mm in diameter) particle delivered to the desired site by minimally invasive means, for instance through capillaries and/or other natural vessels in the body.

Electromagnetic radiation of various frequencies, from very low to optical, can propagate significant distances (e.g. 1-10 cm) in human tissue. However, it attenuates monotonically as it propagates, making it difficult to deliver substantial amounts of power to a localized spot deep within the body (e.g. at depth 5-50 cm) without exceeding the damage thresholds elsewhere. At sufficiently low frequencies (100 MHz and below), electromagnetic fields do not experience significant attenuation on the spatial scale of the cross-section of human body (for example, a typical skin depth for living tissues having electrical conductivity of 1 S/m is about ~50 cm at 1 MHz; respectively, 5 cm at 100 MHz), and thus they can be generated non-invasively at any desired site deep within the body by a contact-free electromagnetic source. However, the extremely long wavelength of electromagnetic radiation at those frequencies makes it difficult to achieve any substantial localization and concentration of electromagnetic energy density at a finite depth. In a homogeneous or nearly-homogeneous medium, local maxima of electromagnetic fields cannot be narrower than roughly one half the wavelength in that medium. At 100 MHz, assuming an average dielectric constant of tissue to be 80, λ/2 is approximately 17 cm. In other words, the entire focus would be comparable or even larger than the cross-section of the organ to be treated. At lower frequencies, minimal attainable focus diameter is even larger. The 1-100 MHz frequency range has the best capacity to penetrate throughout the body without significant attenuation. The 100 MHz-1 GHz range can be potentially used, but for a small subset of ablation tasks, such as for shallow-depth tumors.

To better understand why it is difficult to localize electric field intensity, and consequently the ohmic power dissipation density, in the low-frequency, long-wavelength regime, one may consider that electric field propagation is governed by the Poisson equation, or the source-free Laplace equation away from the sources. A function satisfying Laplace equation is mathematically a harmonic function. One of the fundamental properties of harmonic functions is that they cannot have a maximum at any point inside a domain of definition within which they have no singularities, except at the boundary of said domain. Ultimately, this is the reason why quasistatic electric fields cannot be fully localized with respect to all three dimensions. However, harmonic functions can have a maximum on the boundary of said definition domain. For example, the definition domain can be a spherical shell, such that the domain boundary consists of two disconnected pieces, namely, two spheres of different radii. A local maximum can occur on either of these boundary pieces. We thus arrive at the notion of an embedded perturbing object, whose surface acts as an additional boundary where a quasistatic field maximum can occur.

As another illustrative example, consider an expansion of the source-free electric potential in a spherical domain in terms of the multipole fields. When the spherical domain has no excluded points or excluded volume, any physical field distribution must not have a singularity anywhere in the domain. Consequently, the multipole expansion contains only positive powers of radius, i.e.

$$\Phi(r,\theta,\phi) = \Sigma_{l,m,a}^{\infty} A_{lm}^n r^n Y_{lm}^y(\theta,\phi). \quad \text{(Eq.1)}$$

Observe that in the above expansion, only positive powers of r are allowed, and consequently, the field intensity diminishes towards the center. Now, consider excluding an arbitrarily small volume around the origin (r=0), such that the definition domain becomes a spherical shell. Because of this exclusion, the multipole expansion is now allowed to have terms divergent at r→0, and it generalizes to $$\Phi(r, \theta, \phi) = \sum_{l,m,n}^{\infty} \left( A_{lm}^n r^n + B_{lm}^n \frac{1}{r^{n+1}} \right) Y_{lm}^n(\theta, \phi). \quad \text{(Eq. 2)}$$

It is easy to verify that this function is still a harmonic one. However, now the fields are allowed to grow in intensity towards the inner boundary of the shell. We have thus enabled a field maximum on the inner boundary of the spherical domain. From the perspective of harmonic functional analysis, the existence of this maximum is due to the singularity that exists in the analytical continuation of the function beyond its definition domain. Since this singularity is beyond this domain, it does not need to exist in the physical space.

An embodiment of a system uses small perturbing particles—metallic, dielectric or metamaterial-based—to break the fundamental limits imposed by diffraction laws in quasi-homogeneous media. A configuration proposed here consists of a small particle inside a volume of human tissue, surrounded by an external MARAUC field source, which has no direct contact with the tissue. This model of the system is illustrated by FIG. 1. The volume between the small particle surface and the surface of MARAUC, containing the tissue and some amount of air, can be described as an electromagnetic cavity, which, under proper conditions, would support one or more electromagnetic eigenmodes.

In order to maximize electromagnetic field localization around the small particle, an embodiment includes exciting one of the eigenmodes of the described system at the unitary limit. While many eigenmodes, in particular of dipolar symmetry, can be excited to some extent by plane waves or quasi-uniform fields, the efficiency of their excitation is typically small. For example, the strength of coupling of a uniform field to a dipole eigenmode is given by the dipole strength of the eigenmode, which is proportional to an overlap integral between the eigenmode field profile and the field profile of the excitation. Dipole strength of small particle resonances scales linearly with their volume, and it becomes very small for particles of small diameter. Inefficient coupling leads to poor field localization and poor contrast in the power density, which is an obstacle in using that excitation scheme for tissue-sparing minimally-invasive RF ablation focused at a deep site in the tissue.

On the other hand, if coupling is achieved at the unitary level, or close to the unitary level, the power density profile of the optimum dipolar or multipolar eigenmode of the small particle is produced in the entire system, resulting in excellent contrast between ablative power in the immediate vicinity of the particle, and elsewhere in the tissue.

Notably, a MARAUC field source apparatus enables modes beyond the most commonly considered dipolar field distribution, such as higher-order multipole fields. These fields correspond to the terms with l>1 in Eq.2 above, whereas the dipolar modes are the ones with l=1, and the spherically-symmetric (uniform) illumination corresponds to l=0. As can be seen from Eq.2, higher-order multipole fields decay faster (as a function of radius from the origin) than dipolar fields, thus enabling even higher field localization.

Figure 2A:
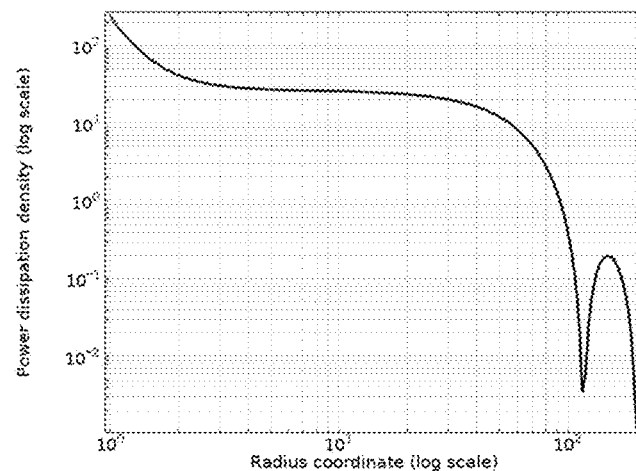
FIG. 2A illustrates a log-log plot of a modeled electric power density profile of a dipolar eigenmode of an embodiment of the modeled system described in conjunction with FIG. 1 suitable for ablating small volumes of tissue.
Figure 2B:
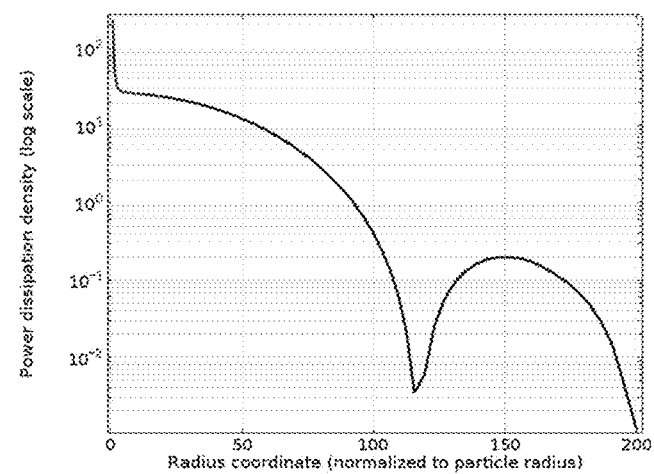
FIG. 2B illustrates a log-linear plot of a modeled electric power density profile of a dipolar eigenmode of an embodiment of the modeled system described in conjunction with FIG. 1 suitable for ablating small volumes of tissue.
Figure 2C:
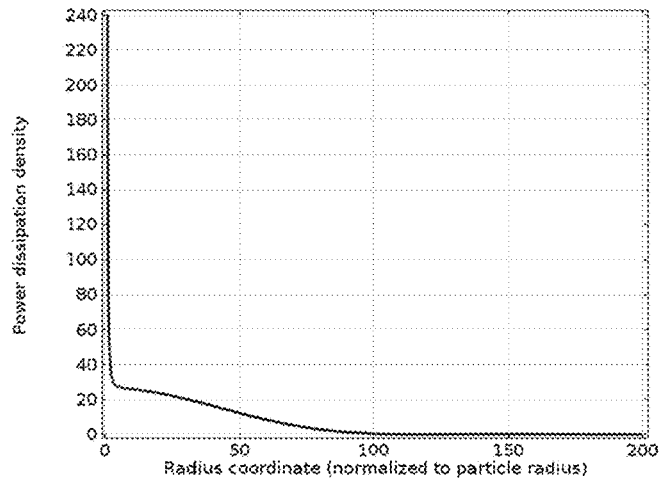
FIG. 2C illustrates a linear-linear plot of a modeled electric power density profile of a dipolar eigenmode of an embodiment of the modeled system described in conjunction with FIG. 1 suitable for ablating small volumes of tissue.

FIGS. 2A-2C illustrate a modeled electric power density profile of a dipolar eigenmode of an embodiment of the modeled system described above suitable for ablating small volumes of tissue (in regions of order 1 mm in diameter). FIG. 2A illustrates a log-log plot of a modeled electric power density profile of a dipolar eigenmode of an embodiment of the modeled system described in conjunction with FIG. 1 suitable for ablating small volumes of tissue. FIG. 2B illustrates a log-linear plot of a modeled electric power density profile of a dipolar eigenmode of an embodiment of the modeled system described in conjunction with FIG. 1 suitable for ablating small volumes of tissue. FIG. 2C illustrates a linear-linear plot of a modeled electric power density profile of a dipolar eigenmode of an embodiment of the modeled system described in conjunction with FIG. 1 suitable for ablating small volumes of tissue. The profiles are shown on a vertical line originating from the center of the particle and traversing through the tissue domain; the profiles lie in the equatorial plane of the dipolar eigenmode where the fields are the strongest.

For concreteness, it was assumed that the mechanism of ablation is local resistive heating of the tissue, whose power dissipation density is given by the standard formula, $Q=\sigma|E|^2$, where $\sigma$ is the local electric conductivity of tissue and $|E|$ is the magnitude of harmonically-modulated electric field. In this example, we observe electric power localization on spatial scale of order 1 diameter of the particle (d=2 mm in this example), where intensity of electric field exceeds its average value in the tissue domain by up to 240 times. The intensity drops down quickly on that scale, and a few particle diameters away from its surface, the intensity stabilizes with a wide plateau, and remains almost uniform throughout the tissue domain. We refer to the intensity on this plateau as the baseline, and normalize the field profiles to it. If the power peak is scaled such that this baseline intensity is slightly below the damage threshold for live cells, cell necrosis would be achieved exclusively in the small region (~1-2 mm) in the immediate vicinity of the particle.

Figure 3:
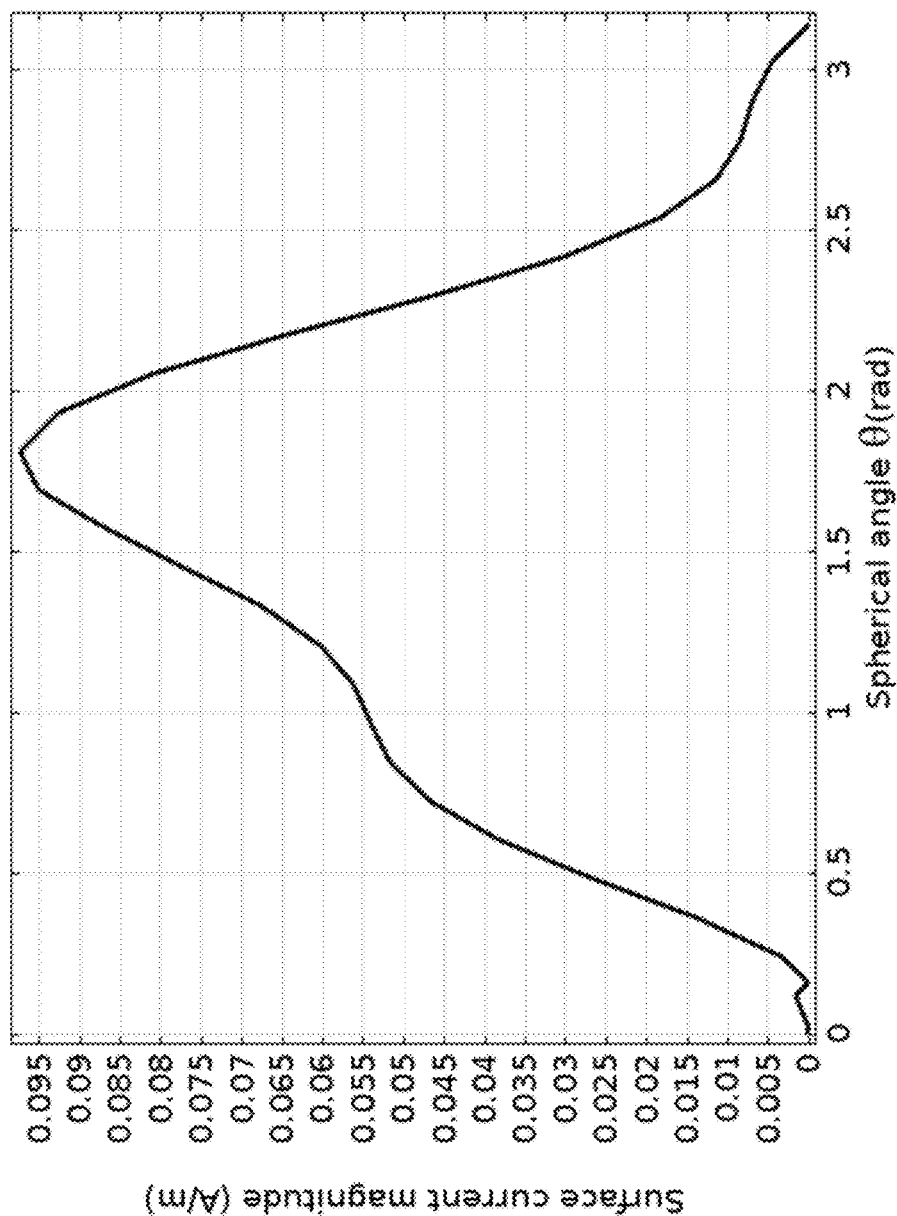
FIG. 3 illustrates a modeled surface current distribution as a function of spherical angle (θ) on a surface that includes a metamaterial aperture with randomly addressable unit cells.

FIG. 3 illustrates a modeled surface current distribution as a function of spherical angle ($\theta$) on a MARAUC surface. For simplicity, in this example the surface current pattern has no azimuthal component and is independent of the azimuthal angle ($\varphi$); this solution corresponds to fields with azimuthal number m=0. Additionally, this particular solution has uniform phase of the surface current, which can be normalized to zero phase.

An embodiment includes an algorithm for calculating the surface current distribution on the surface of MARAUC that leads to optimum coupling to a desired single eigenmode. This inverse problem is solved using an optimization technique, in which the control variables are the magnitudes and phases of surface currents on a closed surface representing the inner surface of a MARAUC. The surface is pixelated into a finite number of finite-area cells, each of which is assumed to have a nearly uniform surface current. As the initial guess for the optimization process, we use the surface current pattern proportional to the electric field distribution of the desired eigenmode to be excited. For simplicity, the surface in the example presented here is assumed to be a sphere, such that efficient axially-symmetric modeling techniques can be employed. The algorithm itself is entirely compatible with an arbitrary-shape closed surface, which does not need to possess spherical or cylindrical symmetry.

Figure 4A:
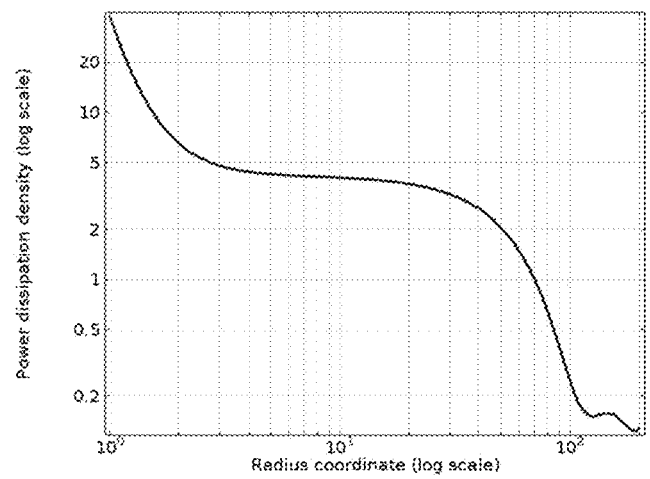
FIG. 4A illustrates a log-log plot of a modeled optimized power dissipation density profile created in the tissue domain resulting from the surface current magnitude and phase of the modeled surface current distribution of FIG. 3.
Figure 4B:
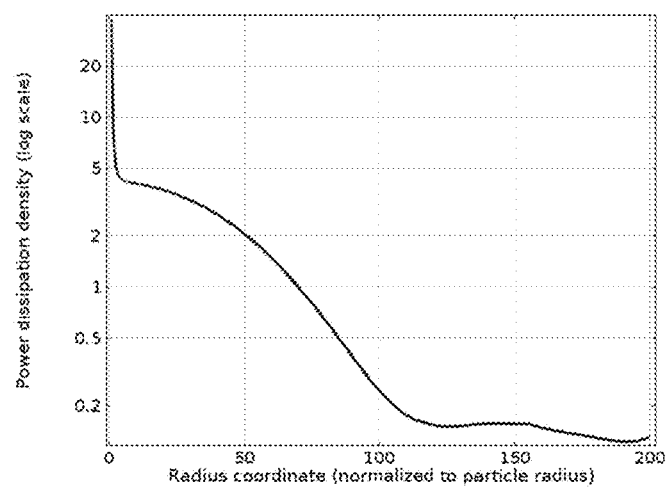
FIG. 4B illustrates a log-linear plot of a modeled optimized power dissipation density profile created in the tissue domain resulting from the surface current magnitude and phase of the modeled surface current distribution of FIG. 3.
Figure 4C:
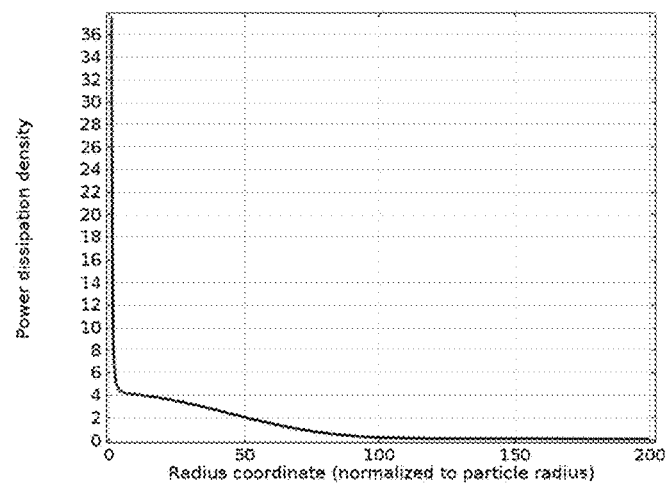
FIG. 4C illustrates a linear-linear plot of a modeled optimized power dissipation density profile created in the tissue domain resulting from the surface current magnitude and phase of the modeled surface current distribution of FIG. 3.

FIGS. 4A-4C illustrate modeled optimized power dissipation density profiles created in the tissue domain resulting from the surface current magnitude and phase of the modeled surface current distribution of FIG. 3. FIG. 4A illustrates a log-log plot of a modeled optimized power dissipation density profiles created in the tissue domain resulting from the surface current magnitude and phase of the modeled surface current distribution of FIG. 3. FIG. 4B illustrates a log-linear plot of a modeled optimized power dissipation density profiles created in the tissue domain resulting from the surface current magnitude and phase of the modeled surface current distribution of FIG. 3. FIG. 4C illustrates a linear-linear plot of a modeled optimized power dissipation density profiles created in the tissue domain resulting from the surface current magnitude and phase of the modeled surface current distribution of FIG. 3.

FIG. 5 illustrates a side by side log-log comparison between the power density profile of a selected dipolar eigenmode of the MARAUC system illustrated by FIG. 2A, and the field distribution produced as a result of an optimized excitation in the MARUAC system illustrated by FIG. 4A.

A method for minimally invasive in vivo thermal ablation is demonstrated above using particles consisting of good electrical conductors. As part of the subject matter, this method can be extended and improved by using different types of particles, including those made of high dielectric constant dielectrics; semiconductors, semimetals and other poor conductors; and electromagnetic metamaterials with engineered dielectric function. In the latter case, negative values of the real part of dielectric function can be obtained at the frequency band of interest. Additionally, the dielectric function of a metamaterial particle can be anisotropic and inhomogeneous (graded). For example, it is known that negative-permittivity particles may support eigenmodes with highly localized electric fields. By choosing the materials and structuring and shaping the particle, spatial power profiles of the sustainable eigenmodes can be manipulated, and optimized to improve specific figures of merit, such as field intensity contrast near/far from the particle, and spatial localization of the highest fields. Examples of strong field localization on the surface of negative-permittivity nano- and micro-objects are described in F. Le, et al., *Metallic Nanoparticle Arrays: A common substrate for both surface-enhanced Raman scattering and surface-enhanced infrared absorption*, 2 ACS Nano 707-718 (2008); G. Shvets & Y. Urzhumov, *Engineering the Electromagnetic Properties of Periodic Nanostructures Using Electrostatic Resonances*, 93 Physical Review Letters 243902 (Dec. 8, 2004); D. Korobkin, et al., *Mid-infrared metamaterial based on perforated SiC membrane: engineering optical response using surface phonon polaritons*, 88 Appl. Phys. A 605-609 (Jun. 12, 2007); and C. Ciraci, et al., *Probing the Ultimate Limits of Plasmonic Enhancement*, 337 Science 1072 (Aug. 31, 2012).

Figure 6:
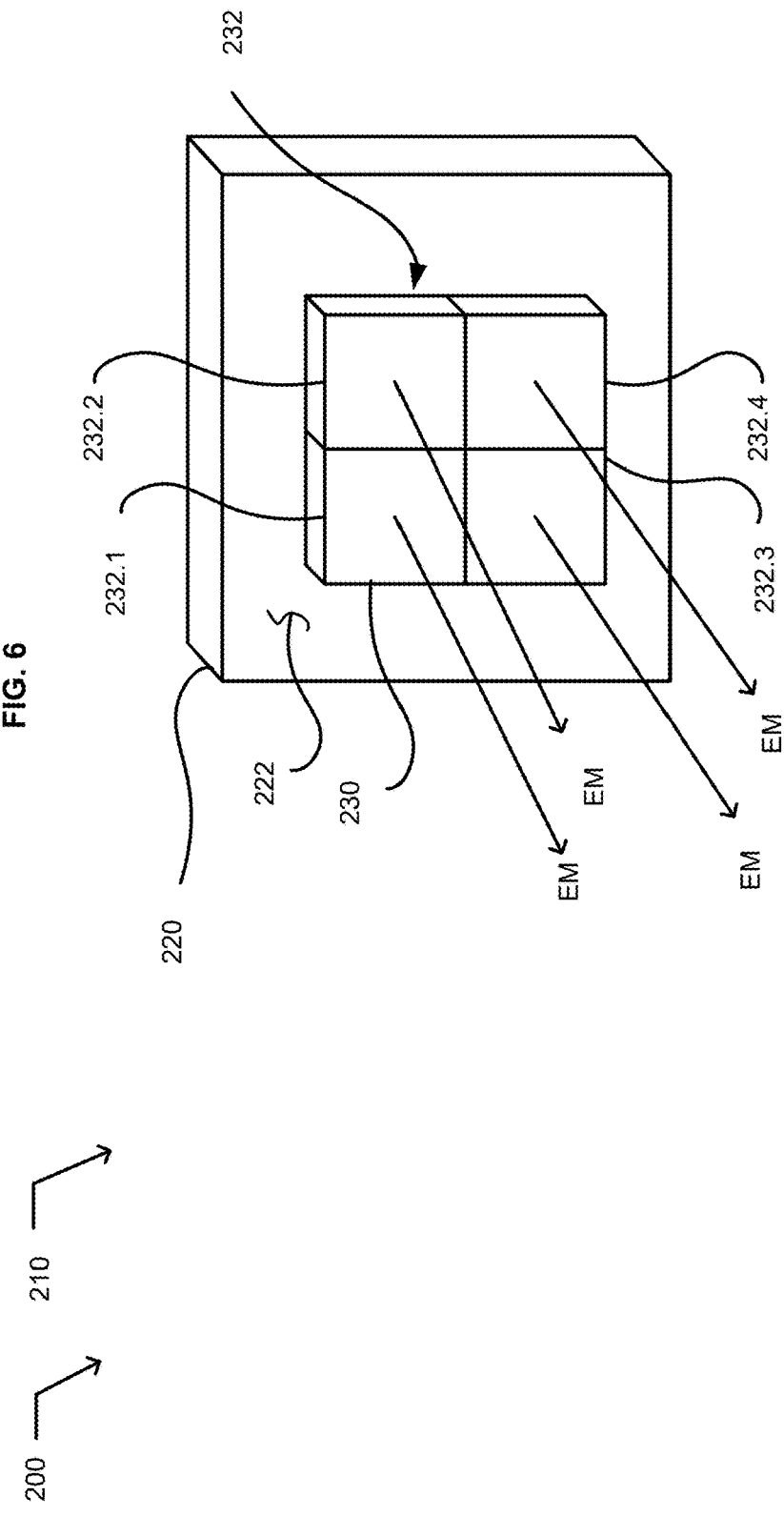
FIG. 6 illustrates aspects of an environment that includes a system.
Figure 7:
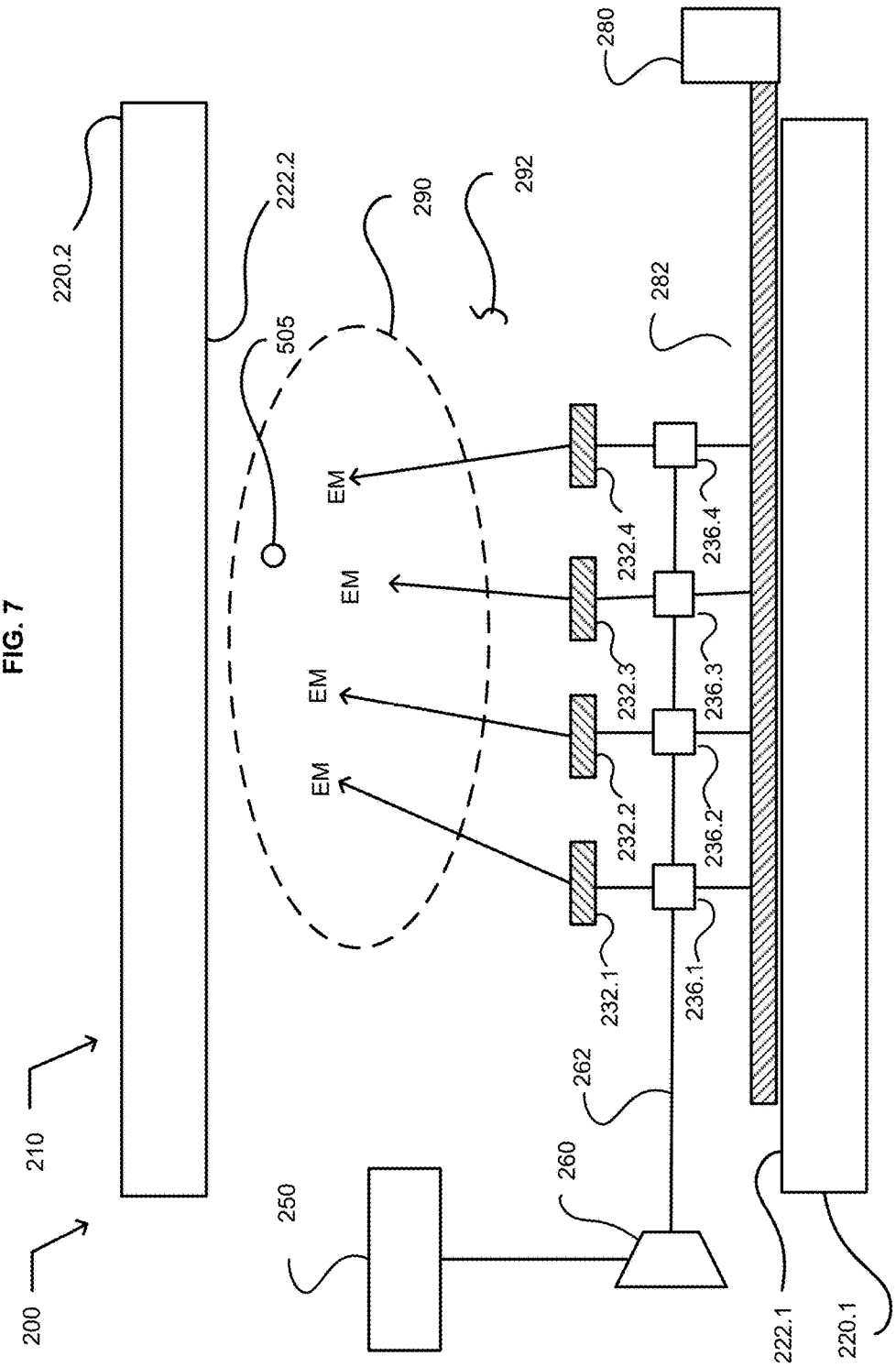
FIG. 7 illustrates additional aspects of the environment and the system of FIG. 6

FIGS. 6 and 7 illustrate aspects of an environment 200 that includes a system 210. The system includes an electromagnetic structure 220 having an inner surface 222 that includes a radiofrequency electromagnetic field source 230. FIG. 7 illustrates an embodiment where the structure includes a first structure 220.1 having a first inner surface 222.1 and a second structure 220.2 having a second inner surface 222.2. The radiofrequency electromagnetic field source includes at least two electronically controllable, artificially structured electromagnetic unit cells 232 configured to create quasi-static radiofrequency electromagnetic fields within a near-field coupling region of the electromagnetic structure. The at least two electronically controllable, artificially structured electromagnetic unit cells are illustrated as unit cells 232.1-232.4. Each of the at least two electronically controllable, artificially structured electromagnetic unit cells is configured to generate a respective electromagnetic field EM. Each unit cell is respectively responsive to a control signal 262. In an embodiment, a quasi-static field is defined as a field that has no wave-like properties. In an embodiment, the near-field region is defined as the area within half-wavelength from all sources.

The system 210 includes a selector circuit 250 configured to select a quasi-static electromagnetic field pattern creating a high contrast radiofrequency electric field 290 in a sub-wavelength electromagnetic cavity 292 defined at least in part by the inner surface 222 of the electromagnetic structure 220 and an exterior surface of a perturbing object 505. The high contrast radiofrequency electric field including a power density localized to a volume adjoining the exterior surface of the perturbing object. In an embodiment, the perturbing object is located within the near-field coupling region of the electromagnetic structure. In an embodiment, the high contrast radiofrequency electric field including a power density localized to a volume surrounding the exterior surface of the perturbing object. In an embodiment, the subwavelength electromagnetic cavity includes a subwavelength electromagnetic resonant cavity defined at least in part by the inner surface of the electromagnetic structure and the exterior surface of the perturbing object.

The system 210 includes a field pattern implementation circuit 260 configured to generate the control signal 262 assigning a respective radiofrequency electromagnetic field characteristic to each of the at least two electronically controllable, artificially structured electromagnetic unit cells 232. The respective assigned radiofrequency electromagnetic field characteristics if implemented by the radiofrequency electromagnetic field source 230 collectively creating the selected quasi-static radiofrequency electromagnetic field pattern within the electromagnetic cavity 292.

In an embodiment, the electromagnetic structure 220 includes an electromagnetic cavity structure. In an embodiment, the electromagnetic structure substantially or partially confines electromagnetic energy within a frequency band. In an embodiment, the electromagnetic structure is dimensioned to at least partially surround at least part of an adult human. For example, the electromagnetic structure may be dimensioned to at least partially surround a chest, abdomen, leg, or head of an adult human. In an embodiment, the electromagnetic structure is electrically insulated from all parts of the human body, by a layer of air or another insulating medium. In an embodiment, the electromagnetic structure and the radiofrequency electromagnetic field source 230 are configured and dimensioned to create quasi-static radiofrequency electromagnetic fields EM converging on the perturbing object 505 such that the sources have a total view angle approaching 4π steradian from the point of view of the perturbing object. In an embodiment, the perturbing object is not physically connected to any exterior part of the system by any artificial conducting path. For example, there are no wires or catheters coupled with the perturbing object. In an embodiment, the electromagnetic structure includes an open electromagnetic cavity structure. In an embodiment, the electromagnetic structure includes a resonant electromagnetic structure. In an embodiment, the electromagnetic structure supports at least two quasi-static radiofrequency electromagnetic field patterns. In an embodiment, the at least two quasi-static radiofrequency electromagnetic field patterns are resonant modes or eigenmodes of the electromagnetic structure.

In an embodiment, the electromagnetic structure 220 includes a parallel plate electromagnetic structure having a first inner surface portion 222.1 and a second parallel inner surface 222.2 portion facing the first inner surface portion. In an embodiment, the first inner surface portion includes first planar inner surface portion, and a second inner surface portion includes a second planar inner surface portion. In an embodiment, the parallel plate electromagnetic structure includes a hollow rectangular parallelepiped electromagnetic structure with at least one open end and an open side. In an embodiment, the electromagnetic structure includes an axisymmetric electromagnetic structure. In an embodiment, the electromagnetic structure has a shortest side ≥100 mm. In an embodiment, the first planar inner surface is separated from the second planar surface by a distance allowing at least a part of a human being to be placed between without touching either the first or second inner surface. In an embodiment, the first planar inner surface is separated from the second planar surface by a distance allowing at least a part of a living vertebrate to be placed between without touching either the first or second inner surface. In an embodiment, the first planar inner surface includes a first arcuate surface and the second planar surface includes a second arcuate surface. In an embodiment, the normal surface vectors of each surface point toward each other. In an embodiment, the first arcuate surface and the second arcuate surface are axisymmetric.

In an embodiment, the inner surface 222 includes an arcuate shape. In an embodiment, the arcuate shape is dimensioned to be positioned around less than 180-degrees of an axis of the inner surface. In an embodiment, the arcuate shape is dimensioned to be positioned around 180-degrees or more of an axis of the inner surface. In an embodiment, the arcuate shape is dimensioned to be positioned around more than 270-degrees of an axis of the inner surface. In an embodiment, the arcuate shape includes two arcuate shaped portions each dimensioned to be positioned around less than 180-degrees of an axis of the inner surface and positioned facing each other across the axis. In an embodiment, the inner surface includes a spherical inner surface. In an embodiment, the spherical inner surface is axisymmetric along a length of the cylindrical electromagnetic structure. In an embodiment, the inner surface includes a cylindrical inner surface.

In an embodiment, the electromagnetic structure 220 includes a hollow rectangular parallelepiped electromagnetic structure with at least one open end. In an embodiment, the hollow rectangular parallelepiped electromagnetic structure includes an axisymmetric hollow rectangular parallelepiped electromagnetic structure. In an embodiment, the shortest side of the axisymmetric hollow rectangular parallelepiped electromagnetic structure is equal to or greater than 50 mm. In an embodiment, the electromagnetic structure includes a hollow cylindrical electromagnetic structure with at least one open end. In an embodiment, the at least one open end has a diameter greater than 50 mm. In an embodiment, the inner surface of the electromagnetic structure includes an arbitrary shape inner surface.

In an embodiment, a first portion of the first inner surface 222.1 includes the radiofrequency electromagnetic field source and a second portion of the second inner surface 222.2 includes a passive surface. In an embodiment, the passive surface includes a conductive material, composite medium, effective medium, metamaterial, or meta-surface. In an embodiment, the passive surface includes a semiconductor material. In an embodiment, the passive surface includes an electromagnetically anisotropic surface. In an embodiment, the electromagnetically anisotropic surface includes an anisotropic surface impedance. In an embodiment, the passive surface includes a soft, a hard, or a soft-and-hard electromagnetic boundary surface imposing boundary conditions on electric and magnetic fields at the passive surface. In an embodiment, the dielectric permittivity value or magnetic permeability value of the passive surface implements an approximation to an electromagnetic soft, hard, or soft-and-hard electromagnetic boundary at the surface of the perturbing object. Embodiments of electromagnetic soft, hard, or soft-and-hard electromagnetic boundary are described by: I. Hannienen et al., *Realization of generalized soft-and-hard boundary*, Progress in Electromagnetics Research, PIER 64, 317-333 (2006); P. Kildal, *Definition of artificially soft and hard surfaces for electromagnetic waves*, Electronics Letters, 4 Feb. 1988, Vo. 24, No. 3; P. Kildal, *Artificially soft and hard surfaces in electromagnetics*, IEEE Transactions on Antennas and Propagation 1537, Vol. 38, No. 10, (October 1990) (all of which are incorporated herein by reference.) In an embodiment, a first portion of the first inner surface includes a transmission line aligned with an axis of the electromagnetic structure and a second portion of the inner surface includes a ground electrode. For example, the transmission line may be connected to a radiofrequency source. In an embodiment, a first portion of the first inner surface includes a micro strip radiofrequency electromagnetic field source aligned with an axis of the electromagnetic structure and a second portion of the second surface includes a ground electrode plane.

In an embodiment, the radiofrequency electromagnetic field source 230 is configured to generate a near-field region electromagnetic field in at least a portion of the 1 MHz-100 MHz range. In an embodiment, the radiofrequency electromagnetic field source is configured to generate a near-field region electromagnetic field in at least a portion of the 100 MHz-300 MHz range. In an embodiment, the radiofrequency electromagnetic field source is configured to generate a near-field region electromagnetic field in at least a portion of the 300 MHz-1 GHz range. In an embodiment, the radiofrequency electromagnetic field source is configured to generate a tunable near-field region quasi-static electromagnetic field. In an embodiment, the tunable near-field region quasi-static electromagnetic field includes a frequency, amplitude, phase, wave impedance, or polarization tunable radiofrequency quasi-static electromagnetic field. For example, wave impedance is the ratio of electric to magnetic field, $Z=E/H$. Only in the near-field can wave impedance be manipulated with a fixed material, both in free space and in any given propagation medium. In an embodiment, the tunable near-field region quasi-static electromagnetic field is tunable over at least a portion of the 1 MHz-100 MHz range. In an embodiment, the tunable near-field region quasi-static electromagnetic field is tunable over at least a portion of the 100 MHz-300 MHz range. In an embodiment, the tunable near-field region quasi-static electromagnetic field is tunable over at least a portion of the 600 MHz-1 GHz range.

In an embodiment, the radiofrequency electromagnetic field source 230 includes at least two spaced apart, electronically controllable, artificially structured electromagnetic unit cells 232. For example, the at least two spaced apart, electronically controllable, artificially structured electromagnetic unit cells may be illustrated by the electromagnetic unit cells 232.1-232.4. In an embodiment, the radiofrequency electromagnetic field source includes at least two electronically controllable and randomly accessible, artificially structured electromagnetic unit cells. In an embodiment, each artificially structured electromagnetic unit cell of the at least two artificially structured electromagnetic unit cells is configured to transform received radiofrequency electromagnetic waves into a radiofrequency electromagnetic field within at least a portion of the electromagnetic structure 220. For example, the radiofrequency electromagnetic waves may be generated by radiofrequency electromagnetic wave generator 280 and conveyed to the artificially structured electromagnetic unit cells by a waveguide 282. In an embodiment, the each artificially structured electromagnetic unit cell of the at least two artificially structured electromagnetic unit cells includes a respective controller 236, illustrated by the controllers 236.1-236.4, configured to regulate electromagnetic fields generated by the respective electromagnetic unit cells in response to the control signal 262. In an embodiment, the controller is configured to regulate a phase, polarization, wave impedance, or amplitude of electromagnetic fields generated by the respective electromagnetic unit cell. For example, in an embodiment, the controller is electronically or digitally switchable between zero attenuation and a selected attention, including 100% attenuation. In an embodiment, the controller is configured to attenuate received radiofrequency electromagnetic waves and convey the attenuated received radiofrequency electromagnetic waves to the respective electromagnetic unit cell. In an embodiment, the controller is configured to amplify received radiofrequency electromagnetic waves and convey the amplified received radiofrequency electromagnetic waves to the respective electromagnetic unit cell. In an embodiment, the controller is electronically switchable between an off-state, and a selected amplification. In an embodiment, the controller includes a variable delay line or a phase-shifter. In an embodiment, the each artificially structured electromagnetic unit cell of the at least two artificially structured electromagnetic unit cells respectively includes a controllable radiofrequency electromagnetic field generator responsive to the control signal and configured to convey the generated radiofrequency electromagnetic waves to the respective electromagnetic unit cell.

In an embodiment, the radiofrequency electromagnetic field source 230 includes at least two groups of at least two electronically controllable, artificially structured electromagnetic unit cells. In an embodiment, each group of the artificially structured electromagnetic unit cells includes at least four artificially structured electromagnetic unit cells. In an embodiment, each group of the artificially structured electromagnetic unit cells includes at least sixteen artificially structured electromagnetic unit cells. In an embodiment, each group of artificially structured electromagnetic unit cells of the at least two groups of artificially structured electromagnetic unit cells includes a respective controller 236 configured to regulate electromagnetic fields generated by the respective electromagnetic unit cells in response to the control signal 262. For example, FIG. 7 illustrates a group of artificially structured electromagnetic unit cells 232.1-232.4 each including a respective controller 236.1-236.4. In an embodiment, each group of the at least two groups of artificially structured electromagnetic unit cells is individually controllable. In an embodiment, each group of the at least two groups of artificially structured electromagnetic unit cells is individually controllable independent of their respective location or sequence in the radiofrequency electromagnetic field source. In an embodiment, each group of the at least two groups of artificially structured electromagnetic unit cells is respectively electronically accessible or controllable. In an embodiment, each group of the at least two groups of artificially structured electromagnetic unit cells includes a respective unit cell controller circuit configured to electronically control a unit cell of the group in response to the characteristic control signal.

In an embodiment, the at least two artificially structured electromagnetic unit cells 232 includes at least two metamaterial unit cells. In an embodiment, the each unit cell of the at least two artificially structured electromagnetic unit cells includes a respective unit cell controller 236 configured to regulate electromagnetic fields generated by the respective electromagnetic unit cell in response to the control signal 262. In an embodiment, a unit cell of the at least two artificially structured electromagnetic unit cells includes an artificially structured metamaterial unit cell with a strong magnetic response. In an embodiment, a unit cell of the at least two artificially structured electromagnetic unit cells includes an artificially structured, highly inductive metamaterial unit cell. In an embodiment, at least two electromagnetic unit cells include at least two sub-wavelength electromagnetic unit cells. In an embodiment, a unit cell of the artificially structured electromagnetic unit cells includes a split ring electromagnetic cavity insert. In an embodiment, the split ring electromagnetic cavity insert is optimized to generate a highly inductive electromagnetic near field. In an embodiment, a unit cell of the artificially structured electromagnetic unit cells includes orthogonally oriented split ring electromagnetic cavity inserts. In an embodiment, the orthogonally oriented split ring electromagnetic cavity inserts are optimized to generate a high inductance density electromagnetic field. In an embodiment, a unit cell of the at least two artificially structured electromagnetic unit cells includes a spiral insert. In an embodiment, the spiral insert is optimized to generate a high inductance density. In an embodiment, the spiral insert includes rectangular or circular spiral insert. In an embodiment, the spiral insert includes at least two planar spirals situated in separate parallel planes and electrically connected to each other to form a three-dimensional meander line. In an embodiment, the three-dimensional meander line includes at least one clockwise oriented spiral and at least one counterclockwise oriented spiral. In an embodiment, a unit cell of the at least two artificially structured electromagnetic unit cells includes a conical helical insert. In an embodiment, the conical helical insert is optimized to generate a high inductance density. In an embodiment, the conical helical insert includes two orthogonally oriented conical helical inserts. In an embodiment, a unit cell of the at least two artificially structured electromagnetic unit cells includes a pyramidal helical insert. In an embodiment, the pyramidal helical insert is optimized to generate a high inductance density. In an embodiment, a unit cell of the at least two artificially structured electromagnetic unit cells includes a sub-wavelength arrangement of magnetic dipole unit cells. In an embodiment, the at least two artificially structured electromagnetic unit cells are each configured to generate a highly inductive electromagnetic near-field. In an embodiment, the at least two artificially structured electromagnetic unit cells are each configured to generate a magnetic field-dominant radiofrequency near-field with magnetic (B) and electric (E) field intensities such that $(B \times c)/E > 1$ (where "c" is the speed of light). In an embodiment, the at least two artificially structured electromagnetic unit cells are each configured to generate a low-wave-impedance radiofrequency near-field with magnetic (H) and electric (E) field intensities such that $E/H < Z_0$ (where $Z_0 = 377$ Ohms). Certain of the above and other embodiments of electromagnetic unit cells are described more fully in U.S. patent application Ser. No. 14/334,368, entitled ARTIFICIALLY STRUCTURED $B_1$ MAGNETIC FIELD GENERATOR FOR MRI AND NMR DEVICES, naming Tom Driscoll, et al. as inventors, filed Jul. 17, 2014. For example, FIG. 3 and portions of the detailed description of that application describe several embodiments of electromagnetic units. That application is incorporated by reference herein, including any subject matter included by reference in that application. In an embodiment, the optimized includes a maximization of the contrast in the power dissipation density in a selected volume adjoining a perturbing object, relative to the power dissipation density averaged over the entire volume within the electromagnetic cavity. In an embodiment, the optimized includes a maximization of the temperature increase in a selected volume adjoining a perturbing object resulting from exposure to electromagnetic fields, subject to a constraint that the temperature elsewhere does not exceed a safe limit. For example, a safe limit may include 39 degrees Celsius. In an embodiment, the optimized includes a maximization of the volume adjoining the perturbing object in which the temperature exceeds a certain threshold level, subject to a constraint that the temperature elsewhere does not exceed a safe limit. For example, a threshold level may include 50° C. For example, a safe limit may include 39° C. In an embodiment, the optimized includes a maximization of the volume adjoining the perturbing object in which the fraction of cells damaged beyond survivability exceeds a certain threshold, subject to a constraint that cell damage probability elsewhere does not exceed a safe limit given the duration of exposure to RF fields. For example, a maximization of the volume adjoining the perturbing object in which cells are damaged beyond survivability exceeds a 90% threshold. For example, the constraint that cell damage probability elsewhere does not exceed a safe limit of 0.001%.

In an embodiment, the selector circuit 250 is configured to select an optimized quasi-static electromagnetic field EM creating a high contrast radiofrequency electric field 290 having a power density localized to a volume adjoining the exterior surface of the perturbing object 505 located within a near-field coupling region of the radiofrequency electromagnetic field source 230.

In an embodiment, the selected optimized high contrast radiofrequency electric field includes a quasi-static electromagnetic field mode of the subwavelength electromagnetic cavity 292 having a high quality factor Q with the perturbing object of at least Q=10. In an embodiment, the high quality factor Q includes a high power transfer efficiency factor. In an embodiment, the quasi-static electromagnetic field mode includes a resonantly coupled mode between the quasi-static electromagnetic field and the perturbing object. In an embodiment, a resonantly coupled mode includes matching a resonant frequency of electromagnetic cavity to the resonant frequency of the perturbing object by changing the quasi-electromagnetic field and maintaining a high Q. In an embodiment, matching a resonant frequency of electromagnetic cavity to the resonant frequency of the perturbing object includes tuning the electromagnetic field coupling with the perturbing object to maintain a high quality factor Q. In an embodiment, matching a resonant frequency of electromagnetic cavity to the resonant frequency of the perturbing object includes maintaining a tuned state if the perturbing object moves. In an embodiment, the selected optimized high contrast radiofrequency electric field includes a high contrast radiofrequency electric field selected by applying a local optimization technique specifying a magnitude and phase of surface currents on a closed surface representing the inner surface of the electromagnetic structure, where the closed surface is pixelated into a finite number of finite-area cells, each of which is assumed to have a nearly uniform surface current proportional to an electric field distribution for an eigenmode of the electromagnetic cavity. In an embodiment, the closed surface includes the radiofrequency electromagnetic field source. In an embodiment, the local optimization technique includes an optimization goal responsive to a numerical forward model of the system. In an embodiment, the numerical forward model of the system includes at least one model of a standardized human body. In an embodiment, the local optimization technique includes an optimization goal responsive to real-time data indicative of an electric field power density or of a temperature of a vertebrate subject in which the perturbing object is implanted.

In an embodiment, the selector circuit 250 is configured to select the quasi-static electromagnetic field pattern responsive to real-time data received from a radiofrequency electromagnetic field sensor. In an embodiment, the radiofrequency electromagnetic field sensor includes a radiofrequency electromagnetic field sensor indicative of a radiofrequency electromagnetic field in a tissue of a vertebrate subject in which the perturbing object is implanted. In an embodiment, the selector circuit is configured to select the quasi-static electromagnetic field pattern responsive to real-time data received from a temperature sensor. In an embodiment, the temperature sensor includes a temperature sensor indicative of a core temperature of a vertebrate subject in which the perturbing object 505 is implanted. In an embodiment, the selector circuit is configured to select the quasi-static electromagnetic field pattern responsive to (i) a parameter of the subwavelength electromagnetic cavity 292, and (ii) a parameter of the perturbing object. In an embodiment, the parameter includes a characteristic, feature, property, or measurable factor useful in defining a behavior. In an embodiment, the parameter of the subwavelength electromagnetic cavity includes a resonant frequency of the subwavelength electromagnetic cavity. In an embodiment, the parameter of the perturbing object includes a shape of the perturbing object. In an embodiment, the parameter of the perturbing object includes a dimension of the perturbing object. In an embodiment, the parameter of the perturbing object includes a surface impedance of the perturbing object. In an embodiment, the parameter of the perturbing object includes a permittivity or permeability of the perturbing object. In an embodiment, a parameter of the perturbing object includes a soft or a hard electromagnetic boundary surface of the perturbing object. In an embodiment, the selector circuit is configured to select a quasi-static electromagnetic field eigenmode of the subwavelength electromagnetic cavity creating the high contrast radiofrequency electric field 290 having a power density localized to a volume adjoining the exterior surface of the perturbing object. In an embodiment, the selector circuit is configured to select a quasi-static electromagnetic field eigenmode of the subwavelength electromagnetic cavity from at least two quasi-static electromagnetic field eigenmodes of the subwavelength electromagnetic cavity. In an embodiment, the selector circuit is configured to select a quasi-static electromagnetic field pattern producing an evanescent coupling an evanescent coupling between the surface of the electromagnetic cavity and the perturbing object. In an embodiment, the selector circuit is configured to select a quasi-static electromagnetic field pattern from at least two quasi-static electromagnetic field patterns producing an evanescent coupling. In an embodiment, the coupling mechanism is mediated through a near-field overlap of the selected non-radiative near-field of the radiofrequency electromagnetic field source and a non-radiative near-field of the perturbing object. For example, a wireless non-radiative energy transfer. In an embodiment, the selected evanescent coupling includes a resonant evanescent coupling. In an embodiment, the selected resonant evanescent coupling creates a high contrast radiofrequency electric field having a power density localized to a volume surrounding and adjoining the exterior surface of the perturbing object.

In an embodiment, the selector circuit 250 is configured to select the quasi-static electromagnetic field pattern in response to a model-based quasi-static electromagnetic field interaction between the inner surface 222 of the electromagnetic structure 220 and the exterior surface of the perturbing object 505. In an embodiment, the selector circuit is configured to select the quasi-static electromagnetic field pattern in response to a model-based estimation of an electric field power density localized to the volume adjoining the exterior surface of the perturbing object. In an embodiment, the model-based estimation is optimized responsive to a set of rules. In an embodiment, the set of rules includes a set of configurable rules.

In an embodiment, the optimized includes a maximization of the contrast in the power dissipation density in a selected volume adjoining a perturbing object, relative to the power dissipation density averaged over the entire volume within the electromagnetic cavity. In an embodiment, the optimized includes a maximization of the temperature increase in a selected volume adjoining a perturbing object resulting from exposure to electromagnetic fields, subject to a constraint that the temperature elsewhere does not exceed a safe limit. For example, the safe limit may be 39° C. In an embodiment, the optimized includes a maximization of the volume adjoining the perturbing object in which the temperature exceeds a certain threshold level, subject to a constraint that the temperature elsewhere does not exceed a safe limit. For example, the certain threshold level may be 50° C. For example, the safe limit may be 39° C. In an embodiment, the optimized includes a maximization of the volume adjoining the perturbing object in which the fraction of cells damaged beyond survivability exceeds a certain threshold, subject to a constraint that cell damage probability elsewhere does not exceed a safe limit, and given the duration of exposure to RF fields. For example, the certain threshold may be 90%. For example, the safe limit may be 0.001%. In an embodiment, the model-based estimation is selected from a best available quasi-static electromagnetic field pattern from at least two available quasi-static electromagnetic field patterns. In an embodiment, the model-based estimation is retrieved from a computer readable storage medium. In an embodiment, the subwavelength electromagnetic cavity 292 comprises the inner surface 222 of the electromagnetic structure 220 and the exterior surface of the perturbing object 505 present at an arbitrary location with respect to the electromagnetic structure 220. In an embodiment, the exterior surface of the perturbing object includes an exterior surface formed by exterior surfaces of two spaced apart perturbing objects or two touching perturbing objects. In an embodiment, the subwavelength electromagnetic cavity supports at least two quasi-static electromagnetic field patterns. For example, the at least two quasi-static electromagnetic field patterns include at least two resonating electromagnetic field patterns or eigenmodes. In an embodiment, the selected quasi-static electromagnetic field pattern includes a selected quasi-static electromagnetic field pattern creating a high contrast radiofrequency electric field having a power density localized to a tissue ablation volume adjoining the exterior surface of the perturbing object. In an embodiment, the selector circuit is configured to select the quasi-static electromagnetic field pattern from a library of at least two quasi-static electromagnetic field patterns creating a high contrast radiofrequency electric field having a power density localized to a volume adjoining the exterior surface of the perturbing object. In an embodiment, the library includes at least two quasi-static electromagnetic field patterns creating a high contrast radiofrequency electric field having a power density localized to a tissue ablation zone adjoining the exterior surface of the perturbing object. In an embodiment, the library includes at least two customized, tailored, adapted, or manufacturer specified quasi-static electromagnetic field patterns creating a high contrast radiofrequency electric field having a power density localized to a tissue ablation zone adjoining the exterior surface of the perturbing object. In an embodiment, the library includes at least two quasi-static electromagnetic field patterns previously established in the subwavelength electromagnetic cavity.

In an embodiment of the system 210, the power density of the selected high contrast radiofrequency electric field 290 includes a first average power density of the radiofrequency electric field in a first volume within 5 mm of the perturbing object 505 that is at least two times greater than a second average power density of the radiofrequency electric field in a second volume between 5 mm and 10 mm of the perturbing object. For example, the first volume may be considered a tissue ablation volume or a tissue ablation zone. For example, the second volume may be considered a tissue sparing volume. For example, a goal of the selected high contrast radiofrequency electric field includes heating a small, defined volume of tissue proximate to the perturbing object by at least 5 degrees Celsius, for example changing the tissue temperature from a normal of 37° C. to 42° C. Some tissues begin to experience damage at temperatures as low as 42° C. Overheating by 20 C is expected to ensure cell mortality given enough exposure time, as normal reaction rates controlling intra- and intercellular metabolic processes change exponentially with the temperature. Overheating by more than $\Delta T=50$-$60°$ C. (leading to temperatures near and above T=100° C.) should be avoided, to prevent boiling and cavitation. On the other hand, cells overheated by less than 5° C. are generally safe. Thus, the temperature contrast between the first volume and the second volume of as little as two degrees C. may be sufficient, five degrees is likely sufficient, and 10-20 degrees is mostly sufficient for medical applications. In an embodiment, the power density of the selected high contrast radiofrequency electric field includes a first average power density of the radiofrequency electric field in a first volume within 2.5 mm of the perturbing object that is at least two times greater than a second average power density of the radiofrequency electric field in a second volume between 2.5 mm and 7.5 mm of the perturbing object. In an embodiment, the power density of the selected high contrast radiofrequency electric field includes a first average power density of the radiofrequency electric field in a first volume within 1 mm of the perturbing object that is at least two times greater than a second average power density of the radiofrequency electric field in a second volume between 1 mm and 5 mm of the perturbing object. In an embodiment, the power density of the selected high contrast radiofrequency electric field includes a first specific absorption rate (SAR) of the radiofrequency electric field in a first volume within 5 mm of the perturbing object that is at least two times greater than a second SAR of the radiofrequency electric field in a second volume between 5 mm and 10 mm of the perturbing object.

In an embodiment, the selector circuit 250 is configured to select a quasi-static radiofrequency electromagnetic field pattern corresponding to a mode of the cavity 292 formed by the interior portion 222 of the structure 220 and the perturbing object 505, and having a coupling efficiency approaching the unitary limit of coupling. For example, a coupling efficiency approaching the unitary limit of coupling may include a coupling efficiency of at least 60%, 75%, 87%, or 95% of the unitary limit of coupling. A coupling strength is proportional to an overlap integral between the eigenmode field profile and the field profile of excitation. In an embodiment, the cavity 292 bounded by the inner surface 222 of the electromagnetic structure 220 and the exterior surface of the perturbing object 505 constitute a three-dimensional topological manifold with a non-connected boundary. In this embodiment, the perturbing object is not connected to any external parts of the system 210. This embodiment differentiates this system from ablation systems where the ablating element sits at the end of a wire, needle or catheter with a transmission line or waveguide inside of it. This embodiment uses tissue proximate to the exterior surface of the perturbing element as passive receiver wirelessly powered by the electric near-fields of the radiofrequency electromagnetic field source 230. This embodiment uses harmless low-frequency quasistatic fields—not propagating waves or focused waves. In an embodiment, the selector circuit is configured to select the quasi-static electromagnetic field EM in response to a parameter of the manifold with a non-connected boundary. For example, the parameter may include a dimension of the manifold, a volume of the manifold, a frequency of a radiofrequency electromagnetic wave fed to the at least two artificially structured electromagnetic unit cells, an eigenmode of the subwavelength electromagnetic cavity, or an eigenmode of the perturbing object. In an embodiment, the selector circuit is configured to select the quasi-static electromagnetic field responsive to (i) a parameter of the manifold with a non-connected boundary and (ii) a parameter of the perturbing object. In an embodiment, the perturbing object is implanted in tissue of a living vertebrate, e.g. a human. In an embodiment, the selector circuit is configured to select the quasi-static electromagnetic field pattern in response to indicia of a core temperature of the living vertebrate. For example, the indicia of a core temperature of the living vertebrate may be provided by a body temperature sensor. For example, the indicia of a core temperature of the living vertebrate may form a baseline plateau in the vertebrate tissue and remainder of the electromagnetic cavity, and allow the power density produced by the selected quasi-static electromagnetic field pattern to be increased or reduced until core temperature rises to a predetermined or preselected level. In an embodiment, the selector circuit is configured to select the quasi-static electromagnetic field pattern in response to a real time feedback loop monitoring a core temperature of the living vertebrate with respect to a specified maximum allowed rise implementing a change in the selected quasi-static electromagnetic field pattern responsive to the monitored core temperature, and evaluating a core temperature change with respect to the change in the selected quasi-static electromagnetic field pattern. For example, the specified maximum allowed rise may be less than 4° C., less than 2° C., or less than another specified maximum allowed rise, to keep under the cell death or blood coagulation temperature limit. In an embodiment, the selector circuit is configured to select the quasi-static electromagnetic field pattern in response to indicia of a power density of the radiofrequency electric field received in tissue of the living vertebrate at a location more than 2 cm away from the perturbing object. For example, the indicia of power density may be received from an electric field sensor. For example, the indicia of power density may form a baseline plateau in the vertebrate tissue and remainder of the electromagnetic cavity, and allow the power density produced by the selected quasi-static electromagnetic field pattern to be increased or decreased until the peripheral power density reaches a maximum safe limit. In an embodiment, the selector circuit is configured to select the quasi-static electromagnetic field pattern in response to a real time feedback loop monitoring an indicia of a power density of the radiofrequency electric field in tissue of the living vertebrate at a location more than 2 cm away from the perturbing object, implement a change in the selected quasi-static electromagnetic field pattern responsive to the monitored indicia of the power density, and evaluate a power density change with respect to the change in the selected quasi-static electromagnetic field pattern. In an embodiment, the selected electromagnetic field pattern creates a high contrast radiofrequency electric field 290 localized to the volume adjoining the exterior surface of the perturbing object 505 and having a power density directly heating tissue of the living vertebrate in the volume adjoining the exterior surface of the perturbing object to a cell damage temperature. In an embodiment, the power density is localized to a volume adjoining the exterior surface of the perturbing object includes a power density directly heating tissue of a living vertebrate adjoining the exterior surface of the perturbing object to cell damage temperature. For example, the localized electric field power density directly heats the adjoining tissue. In an embodiment, the selector circuit is configured to receive data indicative of a change in a spatial relationship between the perturbing object and the inner surface 222, and in response to the received data, select another quasi-static electromagnetic field pattern creating a high contrast radiofrequency electric field having a power density localized to a volume adjoining an exterior surface of a perturbing object with the changed spatial relationship.

Figure 10:
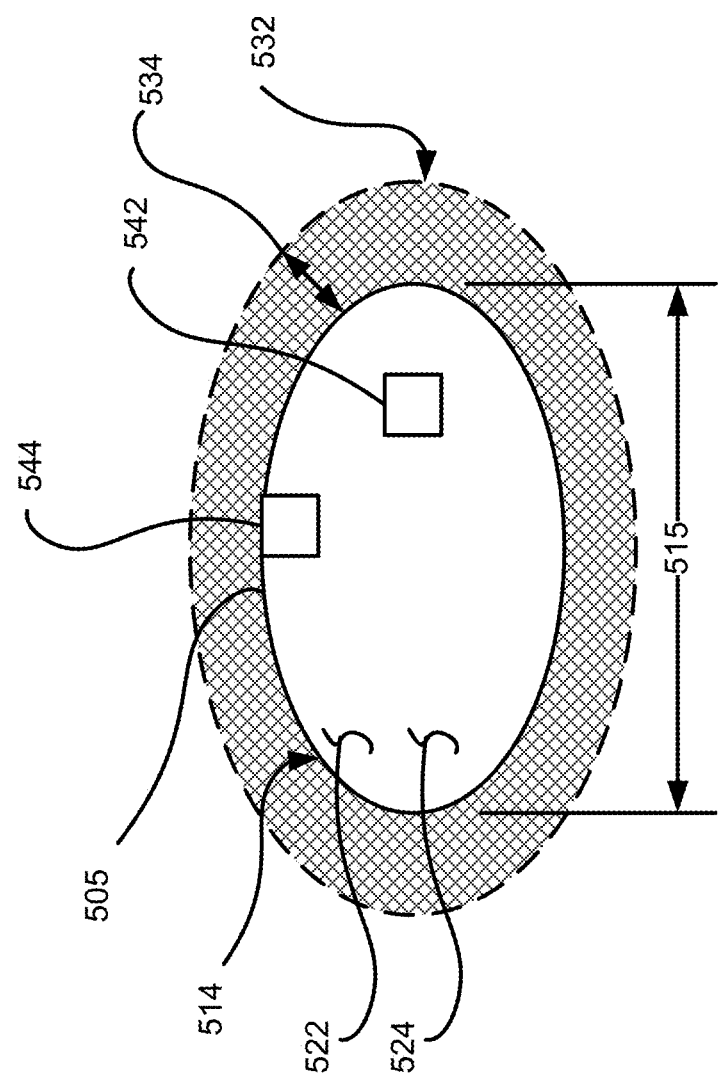
FIG. 10 illustrates an electromagnetic field perturbing object.

FIG. 10 illustrates embodiments of the perturbing object 505 of the system 210. In an embodiment, the perturbing object includes a major dimension 515 that is less than 1 mm. For example, the major dimension may be less than 0.003% of the wavelength of the high contrast radiofrequency electric field 290. In an embodiment, the perturbing object includes a major dimension that is less than 500 microns. In an embodiment, the perturbing object includes a major dimension that is less than 100 microns. In an embodiment, the perturbing object includes biocompatible perturbing object. In an embodiment, the biocompatible perturbing object includes an implantable biocompatible perturbing object. In an embodiment, the biocompatible perturbing object includes an implantable and removable biocompatible perturbing object. In an embodiment, the perturbing object includes biodegradable perturbing object. For example, a biodegradable perturbing object includes anything that will dissipate or metabolize in the body. Examples include high-viscosity liquid droplets, metallic-nanoparticle-loaded oil droplets, a pill loaded with ferromagnetic nanocrystals, etc. There are many different vertebrate organs and locations in which the perturbing object may be situated, ranging in their chemical aggressiveness from pure air (in the lungs), to cerebrospinal fluid, amniotic fluid, lymph, blood serum, saliva, urine, gastric juice, and bile. In an embodiment, the perturbing object includes a minimally invasive implantable perturbing object. For example, minimally invasive may include minimally invasive with respect to blood flow and other physiological functions of a vertebrate, including a human. In an embodiment, the perturbing object includes a strongly-electromagnetic perturbing object. In an embodiment, the perturbing object constitutes an electromagnetic field focusing aide. In an embodiment, the perturbing object comprises a power sink. In an embodiment, the perturbing object includes an electromagnetically resonant perturbing object. For example, an electromagnetically resonant perturbing object may support dipole or multipole resonances of an electric or magnetic nature. In an embodiment, the perturbing object includes perturbing object having an arbitrary permittivity or permeability. In an embodiment, the arbitrary permittivity or permeability does not naturally occur in human beings or living vertebrates. For example, the arbitrary permittivity or permeability may include extrinsic or artificial properties. In an embodiment, the perturbing object includes a local electromagnetic field enhancement object. In an embodiment, the electromagnetic field enhancement is associated with a radiofrequency analog of surface plasmon resonance. For example, the radiofrequency analog of surface Plasmon resonance may be implemented with metamaterials providing negative dielectric permittivity at RF frequencies. In an embodiment, the perturbing object includes a perturbing object having an arbitrary shape. In an embodiment, the exterior surface of the perturbing object includes a highly elongated exterior surface, such as an elongated, rod-like, disk-like or other high aspect-ratio shape. In an embodiment, the exterior surface 514 of the perturbing object includes an arbitrary exterior surface. In an embodiment, the exterior surface of the perturbing object includes a sphere, rectangle, or cylindrical shape. In an embodiment, the exterior surface of the perturbing object includes a selected surface impedance. In an embodiment, the exterior surface of the perturbing object has conductivity greater than 4.0 Siemens per meter at 20° C. For example, copper, aluminum, gold, and silver has conductivity greater than 4.0 Siemens per meter at 20° C.

Continuing with FIGS. 6 and 7, in an embodiment of the field pattern implementation circuit 260, the radiofrequency electromagnetic field characteristic includes a radiofrequency electromagnetic field amplitude characteristic. In an embodiment, the radiofrequency electromagnetic field characteristic includes a radiofrequency electromagnetic field phase characteristic. In an embodiment, the field pattern implementation circuit is configured to generate the control signal 262 assigning a respective radiofrequency electromagnetic field characteristic to a controller 236 of each the at least two electronically controllable, artificially structured electromagnetic unit cells 232. In an embodiment, the radiofrequency electromagnetic field source 230 includes at least two groups of at least two electronically controllable, artificially structured electromagnetic unit cells, and the field pattern implementation circuit is configured to generate a control signal defining a radiofrequency electromagnetic field characteristic respectively assigned to each group of at least two groups of electronically controllable, artificially structured electromagnetic unit cells. In an embodiment, there is no direct physical contact or connection between the radiofrequency electromagnetic field source 220 and the perturbing object 505 or a vertebrate in which the perturbing object is implanted.

In an embodiment, the system 210 includes a radiofrequency electromagnetic wave conducting structure 282 configured to distribute radiofrequency electromagnetic waves to the at least two artificially structured electromagnetic unit cells 232. For example, the radiofrequency electromagnetic waves may be generated by a radiofrequency electromagnetic wave generator or synthesizer 280. In an embodiment, the radiofrequency electromagnetic wave conducting structure is configured to selectively distribute radiofrequency electromagnetic waves to the at least two artificially structured electromagnetic unit cells. In an embodiment, the radiofrequency electromagnetic wave conducting structure configured to distribute radiofrequency electromagnetic waves to controllers 236 of the at least two artificially structured electromagnetic unit cells. In an embodiment, the radiofrequency electromagnetic wave conducting structure includes a transmission line, a waveguide, or other field-confining structure allowing field propagation along at least one of its dimensions. In an embodiment, the waveguide includes a leaky waveguide or another field-propagating structure with a partial field confinement. In an embodiment, the radiofrequency electromagnetic wave conducting structure includes a radiofrequency electrical conductor.

In an embodiment, the system 210 includes the radiofrequency electromagnetic wave generator or synthesizer 280 configured to generate radiofrequency electromagnetic waves in at least a portion of the 1 MHz-1 GHz range.

FIGS. 6 and 7 illustrate an alternative embodiment of the system 210. The alternative embodiment of the system includes a three-dimensional domain having the surface 222 that includes a radiofrequency electromagnetic field source 230. The radiofrequency electromagnetic field source including the at least two electronically controllable, artificially structured electromagnetic unit cells 232, which are configured to create quasi-static radiofrequency electromagnetic fields within the three-dimensional domain, each unit cell respectively responsive to a control signal. The system includes the selector circuit 250 configured to select a quasi-static electromagnetic field pattern creating a high contrast radiofrequency electric field 290 in a subwavelength electromagnetic cavity defined at least in part by the surface 222 of the three-dimensional domain and an exterior surface of a perturbing object 292. The high contrast radiofrequency electric field including a power density localized to a volume adjoining the exterior surface of the perturbing object. The system includes the field pattern implementation circuit 260 configured to generate the control signal 262 assigning a respective radiofrequency electromagnetic field characteristic to each of the at least two electronically controllable, artificially structured electromagnetic unit cells. The respective assigned radiofrequency electromagnetic field characteristics collectively creating the selected quasi-static radiofrequency electromagnetic field pattern within the electromagnetic cavity.

In an embodiment, the three-dimensional domain includes an electromagnetic structure 220. In an embodiment, the electromagnetic structure includes an electromagnetic cavity structure. In an embodiment, the electromagnetic structure includes a subwavelength electromagnetic cavity structure. In an embodiment, the electromagnetic cavity includes a subwavelength electromagnetic cavity. In an embodiment, at least a portion of the surface includes the radiofrequency electromagnetic field source.

Figure 8:
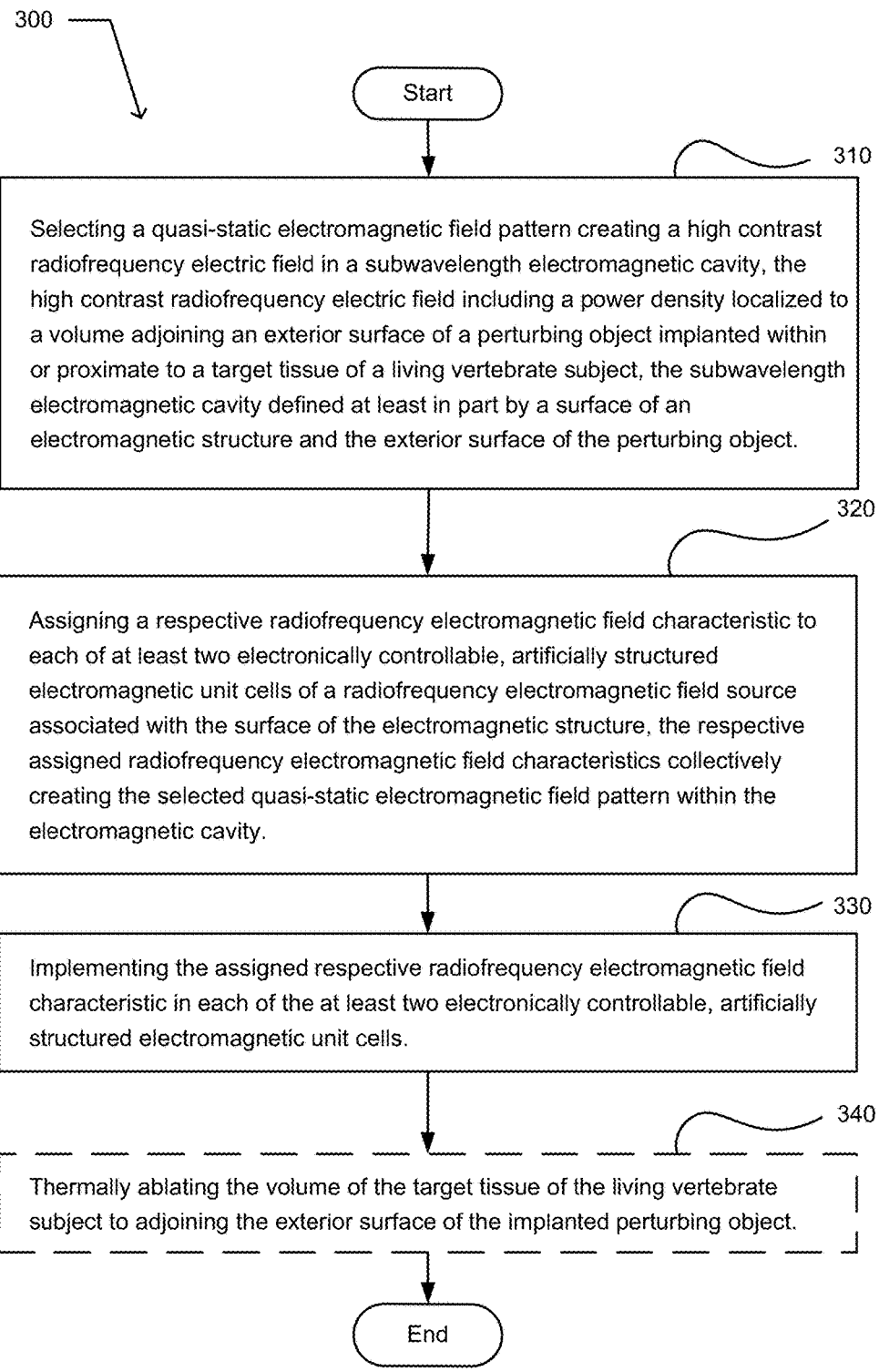
FIG. 8 illustrates an example operational flow.

FIG. 8 illustrates an example operational flow 300. After a start operation, the operational flow includes selection operation 310. The selection operation includes selecting a quasi-static electromagnetic field pattern creating a high contrast radiofrequency electric field in a subwavelength electromagnetic cavity. The high contrast radiofrequency electric field including a power density localized to a volume adjoining an exterior surface of a perturbing object implanted within or proximate to a target tissue of a living vertebrate subject. The subwavelength electromagnetic cavity is defined at least in part by a surface of an electromagnetic structure and the exterior surface of the perturbing object. In an embodiment, the selection operation may be implemented using the selector circuit 250 described in conjunction with FIG. 7. A reproduction operation 320 includes assigning a respective radiofrequency electromagnetic field characteristic to each of the at least two electronically controllable, artificially structured electromagnetic unit cells of a radiofrequency electromagnetic field source associated with the surface of the electromagnetic structure. The respective assigned radiofrequency electromagnetic field characteristics collectively creating the selected quasi-static electromagnetic field pattern within the electromagnetic cavity. In an embodiment, the reproduction operation includes generating a control signal indicating a respective radiofrequency electromagnetic field characteristic assigned to each of at least two electronically controllable, artificially structured electromagnetic unit cells. In an embodiment, the reproduction operation may be implemented using the field pattern implementation circuit 260 described in conjunction with FIG. 7. An execution operation 330 includes implementing the assigned respective radiofrequency electromagnetic field characteristic in each of the at least two electronically controllable, artificially structured electromagnetic unit cells. In an embodiment, the implementing includes implementing in response to the control signal the assigned respective radiofrequency electromagnetic field characteristic in each of the at least two electronically controllable, artificially structured electromagnetic unit cells. In an embodiment, the execution operation may be implemented using the radiofrequency electromagnetic field source 220 described in conjunction with FIGS. 6 & 7. The operational flow includes an end operation.

In an embodiment, the operational flow 300 includes an ablation operation 340 thermally ablating the volume of the target tissue of the living vertebrate subject to adjoining the exterior surface of the implanted perturbing object. In an embodiment, the ablation operation includes directly heating the volume of target tissue with the high contrast radiofrequency electric field in a subwavelength electromagnetic cavity. In an embodiment, the operational flow includes creating the selected quasi-static electromagnetic field pattern. In an embodiment, the creating includes creating the selected quasi-static electromagnetic field pattern and directly heating tissue of the living vertebrate subject adjoining the exterior surface of the perturbing object to an ablation temperature. In an embodiment, the selection operation 310 includes selecting the quasi-static electromagnetic field pattern responsive to (i) a parameter of the subwavelength electromagnetic cavity, and (ii) a parameter of the perturbing object. In an embodiment, the selection operation includes selecting a quasi-static electromagnetic field pattern producing an evanescent coupling between the selected quasi-static electromagnetic field pattern and the perturbing object. In an embodiment, the selection operation includes selecting a quasi-static electromagnetic field pattern creating a high contrast radiofrequency electric field in a subwavelength electromagnetic cavity and having a power density localized to a tissue ablation volume or zone adjoining the exterior surface of the implanted perturbing object. In an embodiment, the operational flow includes distributing radiofrequency electromagnetic waves to the at least two artificially structured electromagnetic unit cells. In an embodiment, the operational flow includes distributing radiofrequency electromagnetic waves having a frequency in at least a portion of the 1 MHz-1 GHz range to the at least two artificially structured electromagnetic unit cells. In an embodiment, the operational flow includes implanting the perturbing object within or proximate to the target tissue of the living vertebrate subject. For example, the implanting may include implanting the perturbing object within 1 mm of the target tissue of the living vertebrate subject. In an embodiment, the operational flow includes positioning a perturbing object within a near-field coupling region of the subwavelength electromagnetic structure having an inner surface that includes the radiofrequency electromagnetic field source.

In an embodiment, the target tissue may include any portion of a vertebrate, including muscle, nerve, epithelial, and connective, brain, or bone tissue.

In an alternative embodiment, an operational flow includes a start operation. After the start operation, the operational flow includes identifying a power density localized to a volume adjoining an exterior surface of a perturbing object implanted within or proximate to a target tissue of a living vertebrate subject. The operational flow includes selecting a quasi-static electromagnetic field pattern creating a high contrast radiofrequency electric field in a subwavelength electromagnetic cavity. The high contrast radiofrequency electric field including the identified power density. The subwavelength electromagnetic cavity is defined at least in part by a surface of an electromagnetic structure and the exterior surface of the perturbing object. The operational flow includes applying electromagnetic field characteristic to each of at least two electronically controllable, artificially structured electromagnetic unit cells of a radiofrequency electromagnetic field source associated with the surface of the electromagnetic structure, the respective assigned radiofrequency electromagnetic field characteristics collectively producing the selected quasi-static radiofrequency electromagnetic field pattern within the electromagnetic cavity.

Figure 9:
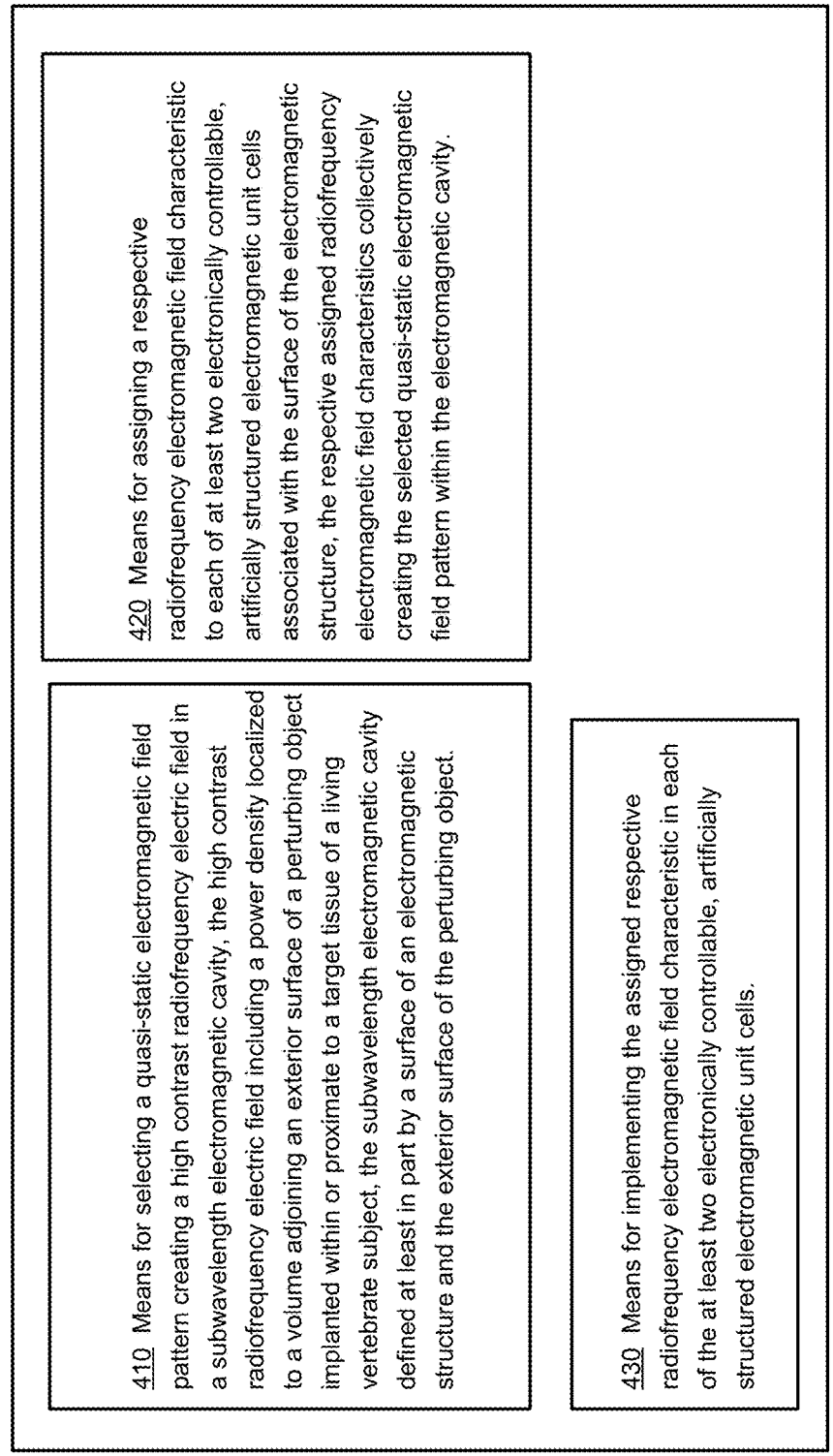
FIG. 9 illustrates another system.

FIG. 9 illustrates a system 400. The system includes means 410 for selecting a quasi-static electromagnetic field pattern creating a high contrast radiofrequency electric field in a subwavelength electromagnetic cavity. The selected high contrast radiofrequency electric field including a power density localized to a volume adjoining an exterior surface of a perturbing object implanted within or proximate to a target tissue of a living vertebrate subject. The subwavelength electromagnetic cavity is defined at least in part by a surface of an electromagnetic structure and the exterior surface of the perturbing object. The system includes means 420 means for assigning a respective radiofrequency electromagnetic field characteristic to each of at least two electronically controllable, artificially structured electromagnetic unit cells associated with the surface of the electromagnetic structure. The respective assigned radiofrequency electromagnetic field characteristics collectively creating the selected quasi-static electromagnetic field pattern within the electromagnetic cavity. In an embodiment, the at least two electronically controllable, artificially structured electromagnetic unit cells comprise a radiofrequency electromagnetic field source. In an embodiment, the means for assigning includes a means for generating a control signal assigning respective radiofrequency electromagnetic field characteristics to each of the at least two electronically controllable, artificially structured electromagnetic unit cells. The system includes means 430 for implementing the assigned respective radiofrequency electromagnetic field characteristic in each of the at least two electronically controllable, artificially structured electromagnetic unit cells. In an embodiment, the means for implementing includes a means for implementing in response to the control signal the assigned respective radiofrequency electromagnetic field characteristic in each of at least two electronically controllable, artificially structured electromagnetic unit cells.

FIG. 10 illustrates an article of manufacture. The article of manufacture includes an electromagnetic field perturbing object 505. The perturbing object includes a biocompatible exterior surface 514. The perturbing object includes a selected dielectric permittivity value 522 or a selected magnetic permeability value 524. The values are selected such that an interaction between the perturbing object and a quasi-static radiofrequency electromagnetic field creates a high contrast radiofrequency electric field having a power density localized to a volume adjoining the biocompatible exterior surface of the perturbing object. In an embodiment, the values are selected such that an interaction between the perturbing object and a quasi-static radiofrequency electromagnetic field in an electromagnetic cavity creates a high contrast radiofrequency electric field having a power density localized to a volume adjoining the biocompatible exterior surface of the perturbing object. For example, FIGS. 6 & 7 illustrate the quasi-static radiofrequency electromagnetic field EM in the electromagnetic cavity 292 creating the high contrast radiofrequency electric field 290 in an interaction with the perturbing object 505 and having a power density localized to a volume adjoining the biocompatible exterior surface of the perturbing object. FIG. 10 illustrates the volume 532 adjoining the biocompatible exterior surface of the perturbing object. In an embodiment, the selected dielectric permittivity value or a selected magnetic permeability value include a dielectric permittivity value or a magnetic permeability value selected to interact with the quasi-static radiofrequency electromagnetic field in the electromagnetic cavity and generate the high contrast radiofrequency electric field having the power density localized to the volume adjoining the biocompatible exterior surface of the perturbing object.

In an embodiment of the perturbing object 505, the selected dielectric permittivity value 522 or the selected magnetic permeability value 524 include a selected complex dielectric permittivity value or a selected complex magnetic permeability value. In an embodiment of the perturbing object, the selected dielectric permittivity value or the selected magnetic permeability value includes a known dielectric permittivity value or magnetic permeability value. In an embodiment, the selected dielectric permittivity value or the selected magnetic permeability value includes a measured dielectric permittivity value or a measured magnetic permeability value. In an embodiment, the selected dielectric permittivity value or the selected magnetic permeability value include the selected dielectric permittivity value and the selected magnetic permeability value. In an embodiment, the quasi-static radiofrequency electromagnetic field in an electromagnetic cavity includes a particular radiofrequency electromagnetic field in an electromagnetic cavity. In an embodiment, the quasi-static radiofrequency electromagnetic field includes a quasi-static radiofrequency electromagnetic field in an electromagnetic cavity.

In an embodiment of the perturbing object 505, the quasi-static radiofrequency electromagnetic field EM in an electromagnetic cavity includes a radiofrequency electromagnetic field having a specified frequency range in an electromagnetic cavity. In an embodiment, the quasi-static radiofrequency electromagnetic field in an electromagnetic cavity includes a selected quasi-static radiofrequency electromagnetic field in an electromagnetic cavity. In an embodiment, the interaction between the perturbing object and the quasi-static radiofrequency electromagnetic field creates a dipole or multi-pole electric or magnetic moment. In an embodiment, the interaction between the perturbing object and the quasi-static radiofrequency electromagnetic field creates a high contrast radiofrequency electric field having a predicted power density localized to a specified volume 532 adjoining the exterior surface 514. In an embodiment, the interaction between the perturbing object and the quasi-static radiofrequency electromagnetic field creates a high contrast radiofrequency electric field having a known power density localized to a specified volume adjoining the exterior surface. In an embodiment, the interaction between the perturbing object and the quasi-static radiofrequency electromagnetic field creates a high contrast radiofrequency electric field having a measured power density localized to a specified volume adjoining the exterior surface (indicated by cross-hatching) surrounding the exterior surface. In an embodiment, the interaction between the perturbing object and the quasi-static radiofrequency electromagnetic field creates a high contrast radiofrequency electric field having a power density localized to a volume closely adjoining the exterior surface. In an embodiment, the volume includes an ablation volume or an ablation zone 534 adjoining the biocompatible exterior surface. In an embodiment, the interaction between the perturbing object and the quasi-static radiofrequency electromagnetic field creates a high contrast radiofrequency electric field having a power density localized to a volume of tissue of a vertebrate subject in which the perturbing object is implanted adjoining the exterior surface. Provide above is additional description of a high contrast radiofrequency electric field.

In an embodiment of the perturbing object 505, the selected dielectric permittivity value 522 is a very high permittivity value ($\varepsilon > 100$) over at least a portion of a 1 MHz-1 GHz frequency range. In an embodiment, the selected dielectric permittivity is substantially higher than the permittivity of water ($\varepsilon \gg 80$) over at least a portion of a 1 MHz-1 GHz frequency range. For example, most vertebrate tissues are permeated with salty water and have electrical properties similar to it. In an embodiment, the selected dielectric permittivity is substantially smaller than the permittivity of water ($\varepsilon \ll 80$) over at least a portion of a 1 MHz-1 GHz frequency range. In an embodiment, the selected dielectric permittivity value is a near zero permittivity value ($-0.1 \leq \varepsilon \leq 0.1$) over at least a portion of a 1 MHz-1 GHz frequency range. In an embodiment, the selected dielectric permittivity value is a negative permittivity value ($\varepsilon < 0$) over at least a portion of a 1 MHz-1 GHz frequency range. In an embodiment, the selected magnetic permeability value 524 is a high permeability value ($\mu > 10$) over at least a portion of a 1 MHz-1 GHz frequency range. In an embodiment, the selected magnetic permeability value is a near zero permeability value ($-0.1 \leq \mu \leq 0.1$) over at least a portion of a 1 MHz-1 GHz frequency range. In an embodiment, the selected magnetic permeability value is negative permeability value ($\mu < 0$) over at least a portion of a 1 MHz-1 GHz frequency range.

In an embodiment, the selected dielectric permittivity value 522 or the selected magnetic permeability value 524 includes a selected exterior surface electric susceptibility value or a selected surface magnetic susceptibility value. For example, a selected negative permeability value may be created by an inclusion of a metamaterial in the surface 514. For example, a selected exterior surface dielectric permittivity value or a selected magnetic permeability value may be created with a high epsilon in the x-direction and $\varepsilon$ near-zero in the y,z-directions, or with $\mu$ near-zero in x,y-directions and $\mu$ near-zero in z-direction. In an embodiment, the selected dielectric permittivity value includes a selected anisotropic dielectric permittivity value. For example, an anisotropic dielectric permittivity value may be a high value, low value, or anisotropic value with at least one component being either high or low. For example, an anisotropic dielectric permittivity value may include what is described as "electromagnetically hard", "soft", and "soft-and-hard". In an embodiment, the magnetic permeability value includes a selected anisotropic magnetic permeability value. In an embodiment, the selected dielectric permittivity value or the selected magnetic permeability value implements an approximation to an electromagnetic soft, hard or soft-and-hard electromagnetic boundary at the surface 514 of the perturbing object 505. Embodiments or examples of soft, hard, and soft and hard surfaces are described above. In an embodiment, the electromagnetic boundary surface of the perturbing object includes surface corrugations. For example, the surface corrugation may include a transverse or longitudinal corrugation, for example, such as transverse or longitudinal relative to the predominant orientation of the electric field vector.

In an embodiment, the perturbing object 505 includes a major dimension 515 less than 1 mm. In an embodiment, the perturbing object includes a major dimension less than 500 microns. In an embodiment, the perturbing object includes a major dimension less than 100 microns. In an embodiment, the perturbing object includes a major dimension less than $\lambda/1,000$, where $\lambda$ is the free-space wavelength of the radiofrequency electromagnetic field. In an embodiment, the perturbing object includes a major dimension less than $\lambda/10,000$.

In an embodiment, the perturbing object 505 includes an implantable biocompatible perturbing object. In an embodiment, the implantable biocompatible perturbing object is removable or biodegradable. In an embodiment, the perturbing object includes a minimally invasive perturbing object. For example, minimally invasive may include minimally invasive with respect to blood flow and other physiological functions of a vertebrate, including a human. In an embodiment, the perturbing object includes a strongly-electromagnetic perturbing object. In an embodiment, the perturbing object constitutes a quasi-static radiofrequency electromagnetic field focusing aide. For example, electromagnetic field focusing can be assisted by a subwavelength power drain effect. Examples of a subwavelength power or perfect drain are described in J. Gonzalez, et al., *Circuital model for the Maxwell Fish Eye perfect drain*, arXiv:1203,2424v1 (physics.optics) (Mar. 12, 2012); F. Sun, et al., *Can Maxwell's fish eye lens really give perfect imaging?* 108 Progress In Electromagnetics Research, 307-322 (2010); Sun, et al., *On subwavelength imaging with Maxwell's fish eye lens*, arXiv: 1009,2814v1 (physics.optics) (Sep. 15, 2010); and J. Gonzalez, et al., *Perfect drain for the Maxwell Fish Eye lens*, 13 New J. Phys. 023038 (Feb. 22, 2011). In an embodiment, the perturbing object includes an electromagnetic resonant perturbing object. For example, the perturbing object may include an electromagnetic dipole or, multipole. In an embodiment, the perturbing object includes a metallic or highly electrically conductive material. For example, the perturbing object may have a surface portion including a metallic or highly electrically conductive material. For example, the perturbing object may have a portion including a metal, semimetal, or semiconductor. In an embodiment, the perturbing object includes a material with a very high dielectric constant ($\varepsilon > 100$), such that $\varepsilon/\varepsilon_{tissue} > 1$. For example, the dielectric constant should be high relative to that of tissues. For water and moist tissues, it is actually about 80, so "high" is therefore larger than 80. For example, a material with a very high dielectric constant may include a paraelectric, ferroelectric, pyroelectric or electretic material, such as strontium titanate, barium strontium titanate, strontium barium niobate, lithium niobate, lithium tantalate, perovskite, and their composites, alloys, and laminates. For example, the material with a very high dielectric constant may provide a strong contrast in E field, such as a large induced current displacement. In an embodiment, the perturbing object includes a material with a relatively low dielectric constant ($\varepsilon < 10$), such that $\varepsilon/\varepsilon_{tissue} < 1$. In an embodiment, the perturbing object includes a metamaterial. For example, the metamaterial may include a micro or nano-structured material having properties not available in nature. For example, a metamaterial may provide a narrow bandwidth high dielectric constant, high magnetic permeability, provide an effective magnetic conductivity, and/or allow a direct control of surface impedance of the particle to maximize contrast in impedance between perturbing object and surrounding tissue. In an embodiment, the perturbing object includes a material with provides $\mu$ near 0, $\mu < 0$, $\varepsilon$ near 0, $\varepsilon < 0$, $\varepsilon \approx \mu \approx 0$, $\varepsilon < 0$ and $\mu < 0$, or $\varepsilon \gg 1$. In an embodiment, the perturbing object includes a local electric field enhancement object. In an embodiment, the local field enhancement is associated with a radiofrequency analog of surface Plasmon resonance. For example, this may be implemented with metamaterials providing negative dielectric permittivity at RF frequencies. In an embodiment, the perturbing object has an arbitrary shape. In an embodiment, the exterior surface of the perturbing object includes a highly elongated exterior surface. In an embodiment, the exterior surface of the perturbing object includes an arbitrary exterior surface. In an embodiment, the exterior surface of the perturbing object includes a sphere, rectangle, or cylindrical shape.

In an embodiment, the exterior surface 514 of the perturbing object 505 includes a selected surface impedance. In an embodiment, the exterior surface of the perturbing object includes a selected anisotropic surface impedance. In an embodiment, the selected anisotropic surface impedance includes an anisotropic surface impedance with at least one component being either large or small compared with the wave impedance of surrounding tissue. In an embodiment, the selected anisotropic surface impedance includes an anisotropic surface impedance with at least one component being either large or small compared with the free-space impedance [$Z_0$=377 Ohm]. In an embodiment, the exterior surface of the perturbing object has a conductivity greater than 4.0 Siemens per meter at 200° C., e.g. titanium, gold, copper, nickel, chrome, aluminum, or silver (only titanium and gold are considered fully biocompatible amongst all metals; other metals can be coated, or we can rely on the short duration of the procedure). In an embodiment, the perturbing object includes high-viscosity liquid droplets, metallic-nanoparticle-loaded oil droplets, or a pill loaded with ferromagnetic nanocrystals.

In an embodiment, the perturbing object 505 further includes a wireless temperature sensor 542. For example, the wireless temperature sensor may include a RFID device with a thermally responsive element and incorporated into the perturbing object. For example, a thermal expansion in a coil of the RFID device will change a resonance frequency in the coil. In an embodiment, the perturbing object further includes a sensor 544 configured to wirelessly transmit data indicative of a characteristic of an electric field at the surface 514 of the perturbing object. In an embodiment, the perturbing object further includes a sensor deriving or receiving operational power from electromagnetic fields at the surface of the perturbing object. For example, the sensor may include a temperature sensor, an electric field sensor, or another sensor. In an embodiment, the perturbing object 505 further includes a micro-electromechanical system (MEMS) deriving or receiving operational power from electromagnetic fields at the surface of the perturbing object and configured to perform a mechanical task. In an embodiment, the mechanical task includes self-propulsion using artificial MEMS cilia for motion through tissues or vesicles. In an embodiment, the mechanical task includes a mechanical cutting of tissue, positioning the perturbing object, or a mechanical manipulation task. For example, the mechanical tasks can implement implantation, re-positioning, and post-operational removal of the perturbing object, or for mechanical assistance in destroying or removing pathological tissue, including the ablated tissue debris.

Figure 11:
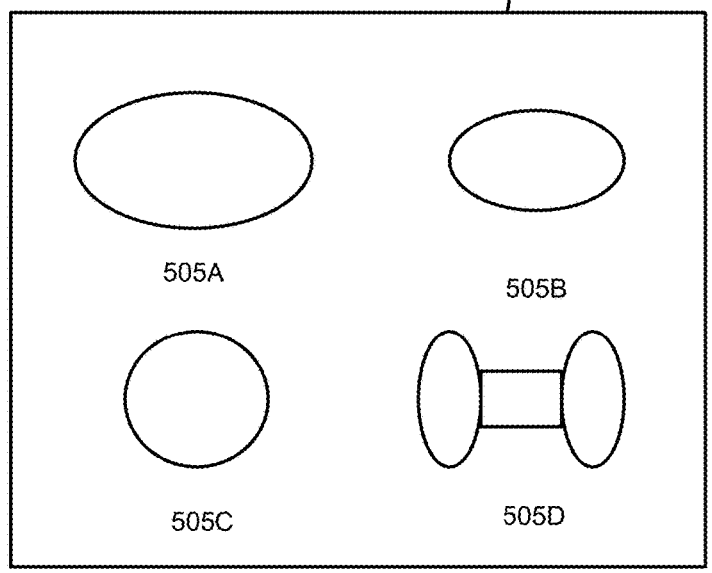
FIG. 11 illustrates an article of manufacture.

FIG. 11 illustrates an article of manufacture 500. The article of manufacture includes an assortment 510 of at least two radiofrequency electromagnetic field perturbing objects 505. The at least two radiofrequency electromagnetic field perturbing objects are illustrated by four different radiofrequency electromagnetic field perturbing objects 505A-505D. Each perturbing object of the at least two radiofrequency electromagnetic field perturbing objects includes a biocompatible exterior surface. For example, see the exterior surface 514 described in conjunction with the perturbing object 505 of FIG. 10. Each perturbing object of the at least two radiofrequency electromagnetic field perturbing objects has a respective selected dielectric permittivity value or a respective selected magnetic permeability value. The values are selected such that an interaction between each perturbing object and a quasi-static radiofrequency electromagnetic field in an electromagnetic cavity creates a high contrast radiofrequency electric field having a respective power density localized to a volume adjoining the biocompatible exterior surface of the perturbing object. FIG. 11 schematically illustrates the respective selected dielectric permittivity value or selected magnetic permeability value of each perturbing object by a different shape. The radiofrequency electromagnetic field perturbing object 505A is schematically illustrated by a spherical shape. Radiofrequency electromagnetic field perturbing object 505B is schematically illustrated by a smaller spherical shape 505B. Radiofrequency electromagnetic field perturbing object 505C is schematically illustrated by an elliptical shape. Radiofrequency electromagnetic field perturbing object 505D is schematically illustrated by a dumbbell shape. While the respective dielectric permittivity value or magnetic permeability value of each perturbing object may be achieved by different exterior surface shapes or sizes in an embodiment, in other embodiments the different dielectric permittivity value or magnetic permeability value of each perturbing object may be achieved by different materials or different exterior surface properties.

Each perturbing object 505A-505D of the at least two radiofrequency electromagnetic field perturbing objects 505 has a respective selected dielectric permittivity value or a respective selected magnetic permeability value. The values are selected such that an interaction between each perturbing object and a quasi-static radiofrequency electromagnetic field in an electromagnetic cavity creates a high contrast radiofrequency electric field having a respective power density localized to a volume adjoining the biocompatible exterior surface of the perturbing object. For example, FIGS. 6 & 7 illustrate the quasi-static radiofrequency electromagnetic field EM in the electromagnetic cavity 292 creating the high contrast radiofrequency electric field 290 in an interaction with the perturbing object 505 and having a power density localized to a volume adjoining the biocompatible exterior surface of the perturbing object. FIG. 10 illustrates the volume 532 adjoining the biocompatible exterior surface 514 of the perturbing object.

The article of manufacture includes information 520 indicative of the power density localized to a volume adjoining the biocompatible exterior surface of the perturbing object of each of the at least two perturbing objects 510. The information may be stored or saved in a volatile or nonvolatile computer storage media product. The computer storage media product may include a magnetic media. The computer storage media product may include a magnetic media, or optical disk, such as a CD or DVD. The computer storage media product may include, but are not limited to, magnetic tape cassettes, memory cards, flash memory cards or drives. The information may be stored or saved on a tangible media, such as on packaging, or on a paper or other writing surface. In an embodiment, the information includes the selected dielectric permittivity value or a selected magnetic permeability value of each of the at least two perturbing objects. In an embodiment, the information includes information indicative of a measured power density localized to a volume adjoining the biocompatible exterior surface of the perturbing object for each of the at least two perturbing objects.

In an embodiment of the at least two radiofrequency electromagnetic field perturbing objects 505, each perturbing object has a respective dielectric permittivity value and a respective magnetic permeability value. In an embodiment, each perturbing object has a respective dielectric permittivity value, magnetic permeability value, or exterior surface area. In an embodiment, the information 520 includes a data sheet describing the dielectric permittivity value or magnetic permeability value of each of the at least two perturbing objects. In an embodiment, the information is indicative of a characteristic of the high contrast radiofrequency electric field creating the power density localized to a volume adjoining an exterior surface for each perturbing object of the at least two perturbing objects.

FIG. 12 illustrates an example operational flow 600. After a start operation, the operational flow includes a placement operation 610. A placement operation 610 includes implanting a selected radiofrequency electromagnetic field perturbing object within or proximate to a target tissue of a living vertebrate subject. The perturbing object is selected from at least two different radiofrequency electromagnetic field perturbing objects. Each perturbing object of the at least two perturbing objects having a biocompatible exterior surface and a respective dielectric permittivity value or a respective magnetic permeability value. The respective values are such that an interaction between a perturbing object and a quasi-static radiofrequency electromagnetic field in a subwavelength electromagnetic cavity creates a high contrast radiofrequency electric field having a different power density localized to a volume adjoining the biocompatible exterior surface of the perturbing object for each of the at least two perturbing objects. For example, a first perturbing object of the at least two perturbing objects may create a first power density within 1 mm of the biocompatible exterior surface of the first perturbing object, and a second perturbing object may create a second power density within 500 microns of the biocompatible exterior surface of the second perturbing object.

A field creation operation 620 includes generating a quasi-static electromagnetic field in the subwavelength electromagnetic cavity selected to create a high contrast radiofrequency electric field having the power density localized to the volume adjoining the exterior surface of the implanted selected perturbing object. In an embodiment, the field creating operation may be implemented using the field pattern implementation circuit 260 and the radiofrequency electromagnetic field source 230 described in conjunction with FIGS. 6 & 7. An ablation operation 630 includes directly heating the target tissue to a cell damage temperature using the power density localized to the volume adjoining the exterior surface of the implanted selected perturbing object. The operational flow includes an end operation.

In an embodiment of the ablation operation 630, the directly heating the target tissue to cell damage temperature further includes directly heating the target tissue to a cell damage temperature using the power density localized to the volume adjoining the exterior surface of the implanted selected perturbing object while not heating other tissue of the living vertebrate to the cell damage temperature.

In an embodiment, the placement operation 610, the implanting includes implanting selected perturbing object within 2 mm of a target tissue of the living vertebrate subject. In an embodiment of the placement operation, the implanting includes implanting selected perturbing object within 1 mm of a target tissue of the living vertebrate subject. In an embodiment of the placement operation, the implanting includes implanting selected perturbing object within a target tissue of the living vertebrate subject.

In an embodiment of the field creation operation 620, the generating includes creating the high contrast radiofrequency electric field having the power density localized to the volume adjoining the exterior surface of the implanted selected perturbing object.

In an embodiment, the operational flow 600 includes positioning the implanted perturbing object within a near-field coupling region of a subwavelength electromagnetic cavity. For example, the location operation may be implemented by positioning the implanted perturbing object, illustrated by the perturbing object 505, within a near-field coupling region of the subwavelength electromagnetic cavity 292 as described in conjunction with FIG. 7. In an embodiment, the operational flow 600 includes selecting the perturbing object from the at least two different radiofrequency electromagnetic field perturbing objects. In an embodiment, the choosing operation may be implemented by choosing a perturbing object from at least two different radiofrequency electromagnetic field perturbing objects 505 described in conjunction with FIG. 11.

FIGS. 6 & 7 illustrate another embodiment of the environment 200 that includes the system 210. The system includes the electromagnetic structure 220 having the inner surface 222 that includes the radiofrequency electromagnetic field source 230. In an embodiment, the electromagnetic structure includes a subwavelength electromagnetic cavity structure. The radiofrequency electromagnetic field source includes at least two electronically controllable, artificially structured electromagnetic unit cells 232 configured to create quasi-static radiofrequency electromagnetic fields EM within a near-field coupling region of the electromagnetic structure. Each unit cell is respectively responsive to the control signal 262.

The system 210 includes a perturbing object 505 implanted within or proximate to a target tissue of a living vertebrate subject, and is located within a subwavelength electromagnetic cavity 292 defined at least in part by the inner surface 222 of the electromagnetic structure 220 and the exterior surface of a perturbing object 505. In an embodiment, the perturbing object is located within a near-field coupling region of the subwavelength electromagnetic cavity. The perturbing object has a biocompatible exterior surface, and a dielectric permittivity value or magnetic permeability value—such that an interaction between the perturbing object and a quasi-static radiofrequency electromagnetic field EM in the electromagnetic cavity creates a high contrast radiofrequency electric field 290 having a power density localized to a volume adjoining the biocompatible exterior surface of the perturbing object. For example, FIGS. 7 & 10 illustrate the high contrast radiofrequency electric field 290 having a power density localized to a volume 532 adjoining the biocompatible exterior surface 514 of the perturbing object 505.

The system 210 includes a selector circuit 250 configured to select a quasi-static electromagnetic field pattern creating a high contrast radiofrequency electric field 290 in the subwavelength electromagnetic cavity 292. The high contrast radiofrequency electric field including a power density localized to a volume adjoining an exterior surface of the perturbing object 505. The system includes a field pattern implementation circuit 260 configured to generate the control signal 262 assigning a respective radiofrequency electromagnetic field characteristic to each of the at least two electronically controllable, artificially structured electromagnetic unit cells 232. If implemented by the radiofrequency electromagnetic field source, the respective assigned radiofrequency electromagnetic field characteristics collectively creating the selected quasi-static radiofrequency electromagnetic field pattern within the electromagnetic cavity.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof.

All references cited herein are hereby incorporated by reference in their entirety or to the extent their subject matter is not otherwise inconsistent herewith.

In some embodiments, "configured" includes at least one of designed, set up, shaped, implemented, constructed, or adapted for at least one of a particular purpose, application, or function.

It will be understood that, in general, terms used herein, and especially in the appended claims, are generally intended as "open" terms. For example, the term "including" should be interpreted as "including but not limited to." For example, the term "having" should be interpreted as "having at least." For example, the term "has" should be interpreted as "having at least." For example, the term "includes" should be interpreted as "includes but is not limited to," etc. It will be further understood that if a specific number of an introduced claim recitation is intended, such an intent will be explicitly recited in the claim, and in the absence of such recitation no such intent is present. For example, as an aid to understanding, the following appended claims may contain usage of introductory phrases such as "at least one" or "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a receiver" should typically be interpreted to mean "at least one receiver"); the same holds true for the use of definite articles used to introduce claim recitations. In addition, even if a specific number of an introduced claim recitation is explicitly recited, it will be recognized that such recitation should typically be interpreted to mean at least the recited number (e.g., the bare recitation of "at least two chambers," or "a plurality of chambers," without other modifiers, typically means at least two chambers).

In those instances where a phrase such as "at least one of A, B, and C," "at least one of A, B, or C," or "an [item] selected from the group consisting of A, B, and C," is used, in general such a construction is intended to be disjunctive (e.g., any of these phrases would include but not be limited to systems that have A alone, B alone, C alone, A and B together, A and C together, B and C together, or A, B, and C together, and may further include more than one of A, B, or C, such as $A_1$, $A_2$, and C together, A, $B_1$, $B_2$, $C_1$, and $C_2$ together, or $B_1$ and $B_2$ together). It will be further understood that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable or physically interacting components or wirelessly interactable or wirelessly interacting components.

With respect to the appended claims the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Use of "Start," "End," "Stop," or the like blocks in the block diagrams is not intended to indicate a limitation on the beginning or end of any operations or functions in the diagram. Such flowcharts or diagrams may be incorporated into other flowcharts or diagrams where additional functions are performed before or after the functions shown in the diagrams of this application. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to one skilled in the art. The various aspects and embodiments disclosed herein are for purposes of illustration and are not intended to be limiting, with the true scope and spirit being indicated by the following claims.

What is claimed is:

1. A system comprising:
a perturbing object configured to be implanted within or proximate to a target tissue of a living vertebrate subject;
an electromagnetic structure having a surface that includes a radiofrequency electromagnetic field source;
the radiofrequency electromagnetic field source including at least two electronically controllable, artificially structured electromagnetic unit cells configured to create quasi-static radiofrequency electromagnetic fields, each unit cell respectively responsive to a control signal;
a selector circuit configured to select a quasi-static electromagnetic field pattern creating a radiofrequency electric field in a subwavelength electromagnetic cavity defined at least in part by the surface of the electromagnetic structure and an exterior surface of the perturbing object, the radiofrequency electric field including a power density localized to a volume adjoining the exterior surface of the perturbing object; and a field pattern implementation circuit configured to:
generate the control signal to which each unit cell is respectively responsive, the control signal assigning a respective radiofrequency electromagnetic field characteristic to each of the at least two electronically controllable, artificially structured electromagnetic unit cells; and transmit the control signal to the at least two electronically controllable, artificially structured electromagnetic unit cells, the respective assigned radiofrequency electromagnetic field characteristics collectively causing the at least two electronically controllable, artificially structured electromagnetic unit cells to create the selected quasi-static radiofrequency electromagnetic field pattern within the subwavelength electromagnetic cavity.

2. The system of claim 1, wherein the electromagnetic structure includes a subwavelength electromagnetic cavity structure.

3. The system of claim 1, wherein the electromagnetic structure substantially or partially confines electromagnetic energy within a frequency band.

4. The system of claim 1, wherein the electromagnetic structure is dimensioned to at least partially surround part of an adult human.

5. The system of claim 1, wherein the at least two electronically controllable, artificially structured electromagnetic unit cells are configured and dimensioned to create quasi-static radiofrequency electromagnetic fields converging on the perturbing object such that the at least two electronically controllable, artificially structured electromagnetic cells define a total view angle approaching 4π steradian from the point of view of the perturbing object.

6. The system of claim 1, wherein the perturbing object is not physically connected to any exterior part of the system by any conducting path.

7. The system of claim 1, wherein the electromagnetic structure supports at least two quasi-static radiofrequency electromagnetic field patterns.

8. The system of claim 1, wherein the electromagnetic structure includes a parallel plate electromagnetic structure having a first surface portion and a parallel second surface portion facing the first surface portion.

9. The system of claim 1, wherein the surface includes an arcuate shape.

10. The system of claim 1, wherein the surface includes a spherical shape.

11. The system of claim 1, wherein a first portion of the surface includes the radiofrequency electromagnetic field source and a second portion of the surface includes a passive surface.

12. The system of claim 1, wherein the radiofrequency electromagnetic field source is configured to generate a near-field region electromagnetic field in a portion of the 100 MHz-300 MHz range.

13. The system of claim 1, wherein the radiofrequency electromagnetic field source is configured to generate a tunable near-field region quasi-static electromagnetic field.

14. The system of claim 1, wherein the radiofrequency electromagnetic field source includes at least two spaced apart, electronically controllable, artificially structured electromagnetic unit cells.

15. The system of claim 1, wherein each artificially structured electromagnetic unit cell of the at least two artificially structured electromagnetic unit cells is configured to transform received radiofrequency electromagnetic waves into a radiofrequency electromagnetic field within at least a portion of the electromagnetic cavity structure.

16. The system of claim 1, wherein each artificially structured electromagnetic unit cell of the at least two artificially structured electromagnetic unit cells includes a respective controller configured to regulate electromagnetic fields generated by the respective electromagnetic unit cell in response to the control signal.

17. The system of claim 1, wherein the radiofrequency electromagnetic field source includes at least two groups of at least two electronically controllable, artificially structured electromagnetic unit cells.

18. The system of claim 1, wherein the at least two artificially structured electromagnetic unit cells includes at least two metamaterial unit cells.

19. The system of claim 1, wherein the at least two artificially structured electromagnetic unit cells are each configured to generate a magnetic field-dominant radiofrequency near-field with magnetic (B) and electric (E) field intensities such that (B×c)/E>1 (where "c" is the speed of light).

20. The system of claim 1, wherein the selector circuit is configured to select an optimized quasi-static electromagnetic field based on a maximization of a temperature increase in a selected volume of tissue adjoining the perturbing object implanted in a vertebrate subject resulting from exposure to electromagnetic fields, subject to a constraint that the temperature elsewhere in the vertebrate subject does not exceed a safe limit.

21. The system of claim 1, wherein the selector circuit is configured to select the quasi-static electromagnetic field pattern responsive to real-time data received from a radiofrequency electromagnetic field sensor indicative of a radiofrequency electromagnetic field in a tissue of a vertebrate subject in which the perturbing object is implanted.

22. The system of claim 1, wherein the selector circuit is configured to select the quasi-static electromagnetic field pattern responsive to real-time data received from a temperature sensor.

23. The system of claim 1, wherein the selector circuit is configured to select the quasi-static electromagnetic field pattern responsive to (i) a parameter of the subwavelength electromagnetic cavity, and (ii) a parameter of the perturbing object.

24. The system of claim 1, wherein the selector circuit is configured to select a quasi-static electromagnetic field pattern producing an evanescent coupling between a wave associated with the surface of the electromagnetic structure and a wave associated with the perturbing object.

25. The system of claim 1, wherein the selector circuit is configured to select the quasi-static electromagnetic field pattern in response to a model-based quasi-static electromagnetic field interaction between the surface of the electromagnetic structure and the exterior surface of the perturbing object.

26. The system of claim 25, wherein the model-based estimation is selected from a best available quasi-static electromagnetic field pattern from at least two available quasi-static electromagnetic field patterns.

27. The system of claim 1, wherein the selector circuit is configured to select the quasi-static electromagnetic field pattern from a library of at least two quasi-static electromagnetic field patterns creating a high contrast radiofrequency electric field having a power density localized to a volume adjoining the exterior surface of the perturbing object.

28. The system of claim 1, wherein the power density of the selected high contrast radiofrequency electric field includes a first average power density of the radiofrequency electric field in a first volume within 5 mm of the perturbing object that is at least two times greater than a second average power density of the radiofrequency electric field in a second volume between 5 mm and 10 mm of the perturbing object.

29. The system of claim 1, wherein the power density of the selected high contrast radiofrequency electric field includes a first specific absorption rate (SAR) of the radiofrequency electric field in a first volume within 5 mm of the perturbing object that is at least 2 times greater than a second SAR of the radiofrequency electric field in a second volume between 5 mm and 10 mm of the perturbing object.

30. The system of claim 1, wherein the selector circuit is configured to select a quasi-static electromagnetic field pattern creating a radiofrequency electric field in the subwavelength electromagnetic cavity corresponding to an eigenmode of the subwavelength electromagnetic cavity.

31. The system of claim 1, wherein the electromagnetic cavity constitute a three-dimensional topological manifold with a non-connected boundary.

32. The system of claim 31, wherein the selector circuit is configured to select the quasi-static electromagnetic field responsive to (i) a parameter of the manifold with non-connected boundary and (ii) a parameter of the perturbing object.

33. The system of claim 1, wherein the power density localized to a volume adjoining the exterior surface of the perturbing object includes a power density directly heating tissue of a living vertebrate adjoining the exterior surface of the perturbing object to a cell damage temperature.

34. The system of claim 1, wherein the selector circuit is configured to receive data indicative of a change in a spatial relationship between the perturbing object and the surface, and in response to the received data, select another quasi-static electromagnetic field pattern creating a high contrast radiofrequency electric field having a power density localized to a volume adjoining an exterior surface of a perturbing object with the changed spatial relationship.

35. The system of claim 1, wherein the perturbing object includes a major dimension that is less than 1 mm.

36. The system of claim 1, wherein the perturbing object includes a perturbing object having a permittivity or permeability that does not naturally occur.

37. The system of claim 1, wherein the radiofrequency electromagnetic field source includes at least two groups of at least two electronically controllable, artificially structured electromagnetic unit cells, and the field pattern implementation circuit is configured to generate a control signal defining a radiofrequency electromagnetic field characteristic respectively assigned to each group of at least two groups of electronically controllable, artificially structured electromagnetic unit cells.

38. The system of claim 1, further comprising:
a radiofrequency electromagnetic wave conducting structure configured to distribute radiofrequency electromagnetic waves to the at least two artificially structured electromagnetic unit cells.

39. A system comprising:
a three-dimensional domain having a surface and a radiofrequency electromagnetic field source;
a perturbing object configured to be implanted within or proximate to a target tissue of a living vertebrate subject;
the radiofrequency electromagnetic field source including at least two electronically controllable electromagnetic unit cells configured to create quasi-static radiofrequency electromagnetic fields within the three-dimensional domain;
a selector circuit configured to select a quasi-static electromagnetic field pattern creating a radiofrequency electric field in an electromagnetic cavity defined at least in part by the surface of the three-dimensional domain and an exterior surface of the perturbing object, the radiofrequency electric field including a power density localized to a volume adjoining the exterior surface of the perturbing object; and
a field pattern implementation circuit configured to:
generate a control signal assigning a respective radiofrequency electromagnetic field characteristic to each of the at least two electronically controllable electromagnetic unit cells; and
transmit the control signal to the at least two electronically controllable electromagnetic unit cells, the respective assigned radiofrequency electromagnetic field characteristics collectively causing the at least two electronically controllable electromagnetic unit cells to create the selected quasi-static electromagnetic field pattern within the electromagnetic cavity.

40. The system of claim 39, wherein the electromagnetic cavity includes a subwavelength electromagnetic cavity.

41. A method comprising:
selecting a quasi-static electromagnetic field pattern creating a radiofrequency electric field in a subwavelength electromagnetic cavity, the radiofrequency electric field including a power density localized to a volume adjoining an exterior surface of a perturbing object implanted within or proximate to a target tissue of a living vertebrate subject, the subwavelength electromagnetic cavity defined at least in part by a surface of an electromagnetic structure and the exterior surface of the perturbing object;
assigning a respective radiofrequency electromagnetic field characteristic to each of at least two electronically controllable, artificially structured electromagnetic unit cells of a radiofrequency electromagnetic field source associated with the surface of the electromagnetic structure, the respective assigned radiofrequency electromagnetic field characteristics collectively creating the selected quasi-static electromagnetic field pattern within the electromagnetic cavity;
implementing the assigned respective radiofrequency electromagnetic field characteristic in each of the at least two electronically controllable, artificially structured electromagnetic unit cells; and
creating the selected quasi-static electromagnetic field pattern.

42. The method of claim 41, further comprising:
thermally ablating the volume of the target tissue of the living vertebrate adjoining the exterior surface of the implanted perturbing object.

43. The method of claim 41, further comprising:
positioning the implanted perturbing object within a near-field coupling region of the electromagnetic structure.

* * * * *